US012624130B2

(12) United States Patent
Nakagawa et al.

(10) Patent No.: US 12,624,130 B2
(45) Date of Patent: May 12, 2026

(54) HYALURONIC ACID DERIVATIVE COMPOSITION, PHARMACEUTICAL COMPOSITION AND HYALURONIC ACID DERIVATIVE-DRUG CONJUGATE COMPOSITION

(71) Applicant: ASAHI KASEI KABUSHIKI KAISHA, Tokyo (JP)

(72) Inventors: Yoshiyuki Nakagawa, Tokyo (JP); Kohei Yabuuchi, Tokyo (JP); Keisuke Fukumoto, Tokyo (JP); Toru Katsumata, Tokyo (JP); Soyeun Yang, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 932 days.

(21) Appl. No.: 17/795,730

(22) PCT Filed: Feb. 5, 2021

(86) PCT No.: PCT/JP2021/004200

§ 371 (c)(1),
(2) Date: Jul. 27, 2022

(87) PCT Pub. No.: WO2021/157677

PCT Pub. Date: Aug. 12, 2021

(65) Prior Publication Data

US 2023/0085879 A1      Mar. 23, 2023

(30) Foreign Application Priority Data

Feb. 5, 2020      (JP) ................................. 2020-018312

(51) Int. Cl.
*C08B 37/08*          (2006.01)
*A61K 47/61*          (2017.01)
(52) U.S. Cl.
CPC .......... *C08B 37/0072* (2013.01); *A61K 47/61* (2017.08)
(58) Field of Classification Search
CPC ................................................. C08B 37/0072
See application file for complete search history.

(56) References Cited

U.S. PATENT DOCUMENTS

| | | |
|---|---|---|
| 2011/0212901 A1 | 9/2011 | Akiyoshi et al. |
| 2015/0231268 A1 | 8/2015 | Nakai et al. |
| 2015/0320873 A1 | 11/2015 | Smejkalova et al. |
| 2015/0352142 A1 * | 12/2015 | Gravett ...................... C08L 5/08 514/54 |
| 2019/0029801 A1 | 1/2019 | Kim et al. |
| 2019/0142959 A1 | 5/2019 | Nakai et al. |
| 2021/0371548 A1 | 12/2021 | Hattori et al. |
| 2023/0066990 A1 | 3/2023 | Yabuuchi et al. |

FOREIGN PATENT DOCUMENTS

| | | | |
|---|---|---|---|
| CA | 2615804 A1 * | 1/2007 | ............ C08F 226/06 |
| CN | 103435718 A | 12/2013 | |
| CN | 104603156 A | 5/2015 | |
| EP | 2 360 188 A1 | 8/2011 | |
| EP | 3 919 072 A1 | 12/2021 | |
| JP | 5-58881 A | 3/1993 | |
| JP | 2001-510150 A | 7/2001 | |
| JP | 2005-139409 A | 6/2005 | |
| JP | 2013-502941 A | 1/2013 | |
| JP | 2016-500130 A | 1/2016 | |
| WO | 99/03452 A1 | 1/1999 | |
| WO | 2010/053140 A1 | 5/2010 | |
| WO | 2011/023355 A2 | 3/2011 | |
| WO | 2014/038641 A1 | 3/2014 | |
| WO | 2014/082609 A1 | 6/2014 | |
| WO | 2017/195880 A1 | 11/2017 | |
| WO | 2019/098393 A1 | 5/2019 | |
| WO | 2020/158771 A1 | 8/2020 | |
| WO | 2021/157665 A1 | 8/2021 | |

OTHER PUBLICATIONS

Masuda, Y. et al., "Synthesis of Silica-Hydrophobized Hyaluronic Acid Hydrid Hydrogel", Lecture proceedings of the Spring Annual Conference of the Chemical Society of Japan, vol. 99, 2019, pp. 1PB-030.

Zhu, Q. et al., "Tumor-Specific Self-Degradable Nanogels as Potential Carriers for Systemic Delivery of Anticancer Proteins", Advanced Functional Materials, vol. 28, 2018, pp. 1707371.

Yamane, S. et al., "Synthesis of Hydrophobized Hyaluronic Acid-Calcium phosphate hybrid fine particle", Lecture proceedings of the Spring Annual Conference of the Chemical Society of Japan, vol. 96, 2016, pp. 2B6-29.

"Regarding Guidelines for Residual Solvents in Pharmaceuticals", Mar. 30, 1998.

International Search Report issued in International Patent Application No. PCT/JP2021/004200, dated Apr. 27, 2021, along with an English translation thereof.

Written Opinion of the International Searching Authority issued in International Application No. PCT/JP2021/004200, dated Apr. 27, 2021, along with an English translation thereof.

Search Report issued in EP Patent Application No. 21751317.5, Jun. 14, 2023.

Qisheng Gu et al. "Hyaluronic acid and clinical medicine", Second Military Medical University Press, pp. 56-57, 2003-11-30, translation.

* cited by examiner

*Primary Examiner* — Bahar Craigo
(74) *Attorney, Agent, or Firm* — GREENBLUM & BERNSTEIN, P.L.C.

(57) ABSTRACT

Provided are: a hyaluronic acid derivative composition that comprises (A) a hyaluronic acid derivative having a steryl group introduced therein; and (B) a polar group-containing compound having at least one functional group selected from the group consisting of hydroxy group, carboxy group, amino group, amide group, carbamate group, urea group and thiol group, wherein the steryl group has been introduced at a ratio of 0.1% or more and less than 35% relative to the hyaluronic acid derivative (A); a pharmaceutical composition that contains the hyaluronic acid derivative composition as a carrier; and a hyaluronic acid derivative-drug conjugate composition wherein, in the hyaluronic acid derivative composition, one or more drugs are conjugated to the hyaluronic acid derivative (A).

6 Claims, 2 Drawing Sheets

HYALURONIC ACID DERIVATIVE COMPOSITION, PHARMACEUTICAL COMPOSITION AND HYALURONIC ACID DERIVATIVE-DRUG CONJUGATE COMPOSITION

TECHNICAL FIELD

The present invention relates to a hyaluronic acid derivative composition, a pharmaceutical composition and hyaluronic acid derivative-drug conjugate composition.

The present application claims priority based on Japanese Patent Application No. 2020-018312 filed in Japan on Feb. 5, 2020, the content of which is incorporated herein by reference.

BACKGROUND ART

In recent years, a bio-pharmaceutical product which is a pharmaceutical product containing protein, peptide or nucleic acid as an active ingredient thereof has been developed for practical use, and the number thereof is increasing every year. The bio-pharmaceutical product can satisfy unmet medical need which cannot be satisfied by conventional low-molecular medicines. However, there are problems in terms of difficulty in absorption from the digestive tract or the mucous membrane as well as low stability in the body and a short half-life in the blood. Thus, a bio-pharmaceutical product requires frequent administration by injection, thereby imposing excessive burdens on both patients and concerned practitioners. Therefore, there is a demand for a drug matrix (sustained-release drug delivery system matrix) which can encapsulate a bio-pharmaceutical product without impairing pharmacological activity and can release an active ingredient gradually in the living body.

From such a background, a sustained-release drug delivery system matrix composed of a hyaluronic acid derivative having excellent safety has been proposed in Patent Document 1. The hyaluronic acid derivative spontaneously associates in an aqueous solution to effectively encapsulate a drug, particularly a bio-pharmaceutical product, while maintaining the biological activity thereof, and aggregates under a physiological saline concentration (or disperses under a physiological saline concentration), and the retention thereof in the blood is favorable. It is stated that, particularly when a bio-pharmaceutical product is used as an active ingredient, the hyaluronic acid derivative may be used as a carrier which can effectively encapsulate a large amount of drug while maintaining a pharmacological activity thereof, or a carrier for sustained release in the blood or a targeting carrier, which exhibits an excellent retention in the blood, and may also serve as a locally (such as subcutaneously) sustained-release carrier which can continuously release a drug.

CITATION LIST

Patent Literature

[PTL 1] PCT International Publication No. WO 2010/053140

SUMMARY OF INVENTION

Technical Problem

However, since it is difficult to control the precipitation forming ability of the hyaluronic acid derivative disclosed in Patent Document 1 depending on salt concentration, and the precipitation forming ability thereof under a physiological saline concentration is not sufficient, there is a risk in which the local retention of a drug composition containing the hyaluronic acid derivative in vivo is impaired.

The present invention has been made in view of the above-mentioned circumstances, and provides a hyaluronic acid derivative composition having an excellent precipitation forming ability under a physiological saline concentration, as well as a pharmaceutical composition using the hyaluronic acid derivative composition, and a hyaluronic acid derivative-drug conjugate composition.

Solution to Problem

The present invention encompasses the following aspects.

(1) A hyaluronic acid derivative composition containing:

a hyaluronic acid derivative (A) in which a steryl group is introduced; and a polar group-containing compound (B) having at least one functional group selected from the group consisting of a hydroxy group, a carboxy group, an amino group, an amide group, a carbamate group, a urea group and a thiol group, wherein the introduction ratio of the steryl group is 0.1% to less than 35% relative to the hyaluronic acid derivative (A).

(2) The hyaluronic acid derivative composition according to (1), wherein the polar group-containing compound (B) is a polar group-containing compound having at least one hydroxy group.

(3) The hyaluronic acid derivative composition according to (1) or (2), wherein the amount of the polar group-containing compound (B) relative to the mass of the hyaluronic acid derivative (A) is 0.001 ppm by mass to less than 1000 ppm by mass.

(4) The hyaluronic acid derivative composition according to any one of (1) to (3), wherein the polar group-containing compound (B) is a compound having plural polar groups.

(5) The hyaluronic acid derivative composition according to any one of (1) to (4), wherein the polar group-containing compound (B) is alcohol.

(6) The hyaluronic acid derivative composition according to (5), wherein the alcohol is selected from the group consisting of ethanol, isopropanol and polyhydric alcohol.

(7) The hyaluronic acid derivative composition according to (6), wherein the alcohol is polyhydric alcohol.

(8) The hyaluronic acid derivative composition according to (7), wherein the alcohol is ethylene glycol.

(9) The hyaluronic acid derivative composition according to any one of (1) to (8), wherein the hyaluronic acid derivative (A) has a repeating unit of the following general formula (I).

In the formula, $R^1$, $R^2$, $R^3$, and $R^4$ are each independently selected from the group consisting of a hydrogen atom, $C_{1-6}$ alkyls, a formyl and $C_{1-6}$ alkylcarbonyls;

Z is a direct bond or a peptide linker consisting of 2 to 30 amino acid residues;

$X^1$ is a group selected from groups of the following formulae:

—$NR^b$—R,

—$NR^b$—COO—R,

—$NR^b$—CO—R,

—$NR^b$—CO—$NR^c$—R,

—COO—R,

—O—COO—R,

—S—R,

—CO—$Y^a$—S—R,

—O—CO—$Y^b$—S—R,

—$NR^b$—CO—$Y^b$—S—R, and

—S—S—R, wherein $R^a$, $R^b$ and $R^c$ are each independently selected from the group consisting of a hydrogen atom, $C_{1-20}$ alkyls, amino $C_{2-20}$ alkyls and hydroxy $C_{2-20}$ alkyls, wherein a group selected from the group consisting of —O— and —$NR^f$— may be inserted in an alkyl moiety thereof;

$R^f$ is selected from the group consisting of a hydrogen atom, $C_{1-12}$ alkyls, amino $C_{2-12}$ alkyls and hydroxyl $C_{2-12}$ alkyls, wherein a group selected from the group consisting of —O— and —NH— may be inserted in an alkyl moiety thereof;

R is a steryl group;

Y is a $C_{2-30}$ alkylene, or —$(CH_2CH_2O)_m$—$CH_2CH_2$—, and a group selected from the group consisting of —O—, —$NR^g$— and —S—S— may be inserted in the alkylene;

$R^g$ is selected from the group consisting of a hydrogen atom, $C_{1-20}$ alkyls, amino $C_{2-20}$ alkyls and hydroxy $C_{2-20}$ alkyls, wherein a group selected from the group consisting of —O— and —NH— may be inserted in an alkyl moiety thereof;

$Y^a$ is a $C_{1-5}$ alkylene;

$Y^b$ is a $C_{2-8}$ alkylene or a $C_{2-8}$ alkenylen; and m is an integer of 1 to 100.

(10) The hyaluronic acid derivative composition according to (9), wherein R is a cholesteryl group.

(11) The hyaluronic acid derivative composition according to any one of (1) to (10), wherein the molecular weight of the hyaluronic acid derivative (A) is 1,000 to less than 1,000,000.

(12) A pharmaceutical composition containing: a drug; and a carrier, wherein the carrier is the hyaluronic acid derivative composition of any one of (1) to (11).

(13) The pharmaceutical composition according to (12), wherein the drug forms a complex with the hyaluronic acid derivative (A).

(14) The pharmaceutical composition according to (12) or (13), wherein the drug is a pharmacologically active protein, a peptide or a nucleic acid.

(15) A hyaluronic acid derivative-drug conjugate composition containing: the hyaluronic acid derivative composition of any one of (1) to (11); and at least one drug, wherein at least one drug is conjugated to the hyaluronic acid derivative (A) in the hyaluronic acid derivative composition.

Advantageous Effects of Invention

The hyaluronic acid derivative composition according to the above-mentioned embodiment makes it possible to provide a hyaluronic acid derivative composition having an excellent precipitation forming ability under a physiological saline concentration, as well as a pharmaceutical composition containing the same, and a hyaluronic acid derivative-drug conjugate composition.

DESCRIPTION OF EMBODIMENTS

Figure 1:
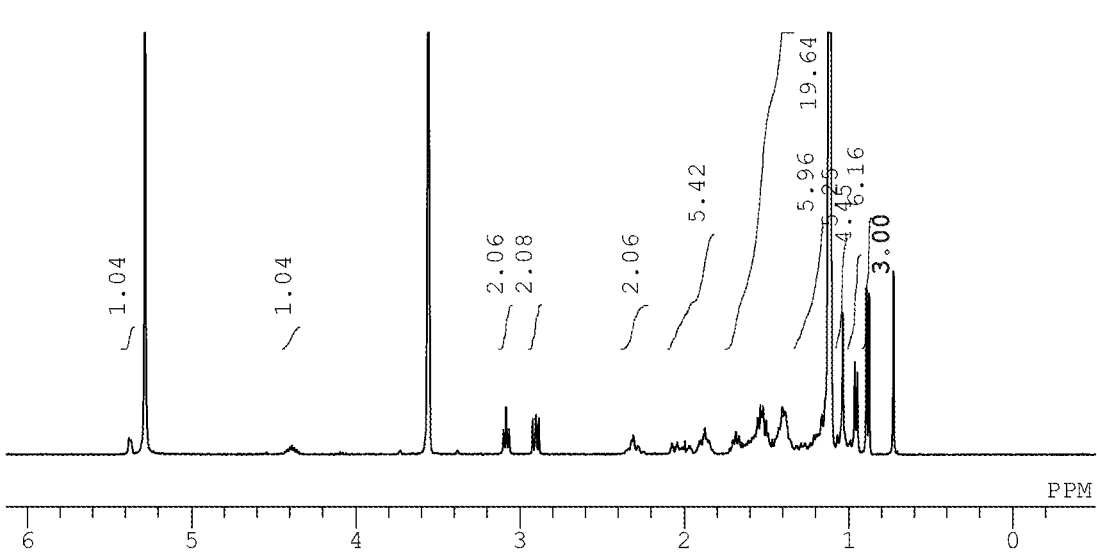
FIG. 1 is $^1$H-NMR spectrum of cholesteryl 6-aminohexylcarbamate hydrochloride in Example 1.

Although an embodiment according to the present invention (hereinafter, abbreviated as "present embodiment") will be explained in detail below, the present invention is not limited thereto, and may be modified variously within the gist thereof.

Terms used in the present specification will be explained below.

The term "$C_{1-20}$ alkyl" used in the present specification means a linear or branched alkyl group having 1 to 20 carbon atoms, and examples thereof include "$C_{1-4}$ alkyls" such as methyl, ethyl, n-propyl, iso-propyl, n-butyl, sec-butyl, iso-butyl, and tert-butyl, and further include n-pentyl, 3-methylbutyl, 2-methylbutyl, 1-methylbutyl, 1-ethylpropyl, n-hexyl, 4-methyl pentyl, 3-methylpentyl, 2-methylpentyl, 1-methylpentyl, 3-ethylbutyl, and 2-ethylbutyl. The term "$C_{1-20}$ alkyl(s)" encompasses $C_{1-12}$ alkyls having 1 to 12 carbon atoms and $C_{1-6}$ alkyl groups having 1 to 6 carbon atoms.

The term "$C_{1-6}$ alkylcarbonyl" used in the present specification means an alkylcarbonyl group in which an alkyl moiety is a $C_{1-6}$ alkyl mentioned above, and examples thereof include "$C_{1-4}$ alkylcarbonyl" such as acetyl, propionyl, n-propylcarbonyl, iso-propylcarbonyl, n-butylcarbonyl, sec-butylcarbonyl, iso-butylcarbonyl, and tert-butylcarbonyl.

The term "amino $C_{2-20}$ alkyl" used in the present specification means a linear or branched alkyl having an amino group as a substituent and having 2 to 20 carbon atoms, wherein, for example, the amino group may be positioned on a carbon atom at a terminal of the alkyl group. The term "amino $C_{2-20}$ alkyl" encompasses amino $C_{2-12}$ alkyl having 2 to 12 carbon atoms.

The term "hydroxyl $C_{2-20}$ alkyl" used in the present specification means a linear or branched alkyl group having a hydroxy group as a substituent and having 2 to 20 carbon atoms, wherein, for example, the hydroxyl group may be positioned on a carbon atom at a terminal of the alkyl group. The term "hydroxy $C_{2-20}$ alkyl" encompasses hydroxy $C_{2-12}$ alkyl having 2 to 12 carbon atoms.

The term "$C_{2-30}$ alkylene" used in the present specification means a linear or branched divalent saturated hydrocarbon group having 2 to 30 carbon atoms, and examples thereof include ethylene and propylene, as well as $C_{2-20}$ alkylenes having 2 to 20 carbon atoms, $C_{2-8}$ alkylenes having 2 to 8 carbon atoms, and groups of "—$(CH_2)_n$—" (wherein n is 2 to 30, preferably 2 to 20, and more preferably 2 to 15).

The term "$C_{1-5}$ alkylene" used in the present specification means a linear or branched divalent saturated hydrocarbon group having 1 to 5 carbon atoms, and examples thereof include methylene, ethylene, and propylene.

The term "$C_{2-8}$ alkenylen" used in the present specification means a linear or branched divalent saturated hydrocarbon group having 2 to 8 carbon atoms and including at least one double bond, and examples thereof include —CH=CH—, —C(CH$_3$)=CH—, 2-butene-1,4-diyl, hepta-2,4-diene-1,6-diyl, and octa-2,4,6-triene-1,8-diyl. In a case where geometrical isomerism exists, their isomers and mixtures thereof are also included.

<<Hyaluronic Acid Derivative Composition>>

A hyaluronic acid derivative composition according to the present embodiment contains: a hyaluronic acid derivative (A) in which a steryl group is introduced (hereinafter, may be referred to as "hyaluronic acid derivative (A)"); and a polar group-containing compound (B) having at least one functional group selected from the group consisting of a hydroxy group, a carboxy group, an amino group, an amide group, a carbamate group, a urea group and a thiol group. The introduction ratio of steryl group relative to the hyaluronic acid derivative (A) is 0.1% to less than 35%.

The hyaluronic acid derivative composition according to the present embodiment can control the precipitation forming ability depending on salt concentration and dissolve at a low salt concentration, whilst enhances the precipitation forming ability under a physiological saline concentration by allowing the polar group-containing compound (B) having at least one functional group selected from the group consisting of a hydroxy group, a carboxy group, an amino group, an amide group, a carbamate group, a urea group and a thiol group to serve as an aggregation enhancer under a physiological saline concentration against the hyaluronic acid derivative (A) having an introduction ratio of steryl group within the above-mentioned range. The term "physiological saline concentration" used herein means the salt concentration at an administration site of an animal to be administered. For example, the physiological saline concentration in human corresponds to a concentration of 150 mM sodium chloride. The term "low salt concentration" means a concentration sufficiently lower than the physiological saline concentration.

<Hyaluronic Acid Derivative (A) in which a Steryl Group is Introduced>

In the hyaluronic acid derivative (A), a steryl group may be bonded to a hyaluronic acid directly or via a linker.

Although an arbitrary peptide linker or synthetic compound linker that can be introduced by genetic engineering may be used as the "linker" used herein, a peptide linker is preferable in the hyaluronic acid derivative (A) according to the present embodiment. Although the length of the peptide linker is not particularly limited and can be chosen by one of ordinary skill in the art depending on the purpose, the preferable length is 2 amino acids or more (although the upper limit thereof is not particularly limited, the length is usually 30 amino acids or less, and preferably 20 amino acids or less), and particularly preferably 15 amino acids. As peptide linkers included in the hyaluronic acid derivative (A), peptide linkers each having the same length, or peptide linkers each having different lengths may be used.

[Steryl Group]

The term "steryl group" used in the present specification is not particularly limited, provided that the group has a steroid skeleton. Specific examples of steroid include cholesterol, cholestanol, campestanol, ergostanol, stigmastanol, coprostanol, stigmasterol, sitosterol, lanosterol, ergosterol, simiarenol, bile acid, testosterone, estradiol, progesterone, cortisol, cortisone, aldosterone, corticosterone, and deoxycorticosterone. Examples of a steryl group include a cholesteryl group, a stigmasteryl group, a lanosteryl group, and an ergosteryl group, and among these, a cholesteryl group (especially, cholesta-5-ene-3β-yl group) is preferable.

[Introduction Ratio of Steryl Group]

The introduction ratio of steryl group relative to the hyaluronic acid derivative (A) (hereinafter, may be referred to as "introduction ratio of steryl group" simply) is 0.1% to less than 35%, preferably 5% to 33%, more preferably 6% to 22%, and even more preferably 6% to 20%.

Since the introduction ratio of steryl group is within the above-mentioned range, the hyaluronic acid derivative becomes to have a property in which the hyaluronic acid derivative dissolves favorably in pure water or under a low salt concentration but aggregates to form a precipitate under a physiological saline concentration. The introduction ratio of steryl group within the above-mentioned range can bring a hyaluronic acid derivative-drug conjugate composition in which a drug is conjugated to the hyaluronic acid derivative (A) in the hyaluronic acid derivative composition into a precipitation-type sustained-release formulation that takes advantage of the feature of aggregation after administration, when the hyaluronic acid derivative-drug conjugate composition is administered in the body (administered subcutaneously, for example).

The introduction ratio of steryl group can be measured by $^1$H-NMR measurement in accordance with the method described in below examples. Namely, the introduction ratio can be calculated from an integrated value of a peak derived from steryl group of the hyaluronic acid derivative (A) in the $^1$H-NMR spectrum of the hyaluronic acid derivative composition and an integrated value of a peak derived from acetyl group of N-acetyl-D-glucosamine contained in the hyaluronic acid derivative (A) (COCH$_3$, 1.6 ppm to 2.0 ppm, 3H) in accordance with the following equation.

$$[\text{Introduction ratio of steryl group (\%)}] = [(\text{Integrated value of a peak derived from steryl group of the hyaluronic acid derivative(A)})/(\text{Integrated value of a peak derived from acetyl group of N-acetyl-D-glucosamine})] \times 100$$

In a case where a steryl group is a cholesteryl group, the introduction ratio of steryl group is specifically calculated from an integrated value of a peak derived from acetyl group of N-acetyl-D-glucosamine (COCH$_3$, 1.6 ppm to 2.0 ppm, 3H) and an integrated value of a peak derived from methyl group of a cholesteryl group (CH$_3$, 0.7 ppm, 3H). Since a peak derived from cholestery group (5H) overlaps peaks including a peak derived from acetyl group of N-acetyl-D-glucosamine around 1.6 ppm to 2.0 ppm, a value obtained by subtracting 5/3 of an integrated value of a peak derived from methyl of cholesteryl group (0.7 ppm) from an integrated value of peaks around 1.6 ppm to 2.0 ppm (i.e., integrated value (1.6 ppm to 2.0 ppm)–integrated value (0.7 ppm)×5/3) is used as an integrated value of a peak derived from acetyl group of N-acetyl-D-glucosamine.

$$[\text{Introduction ratio of steryl group (\%)}] = [(\text{Integrated value of a peak derived from methyl group of cholesteryl group})/(\text{Integrated value of a peak derived from acetyl group of N-acetyl-D-glucosamine})] \times 100 = [\text{integrated value}(0.7 \text{ ppm})/\{\text{Integrated value}(1.6 \text{ ppm to } 2.0 \text{ ppm})–\text{Integrated value}(0.7 \text{ ppm}) \times 5/3\}] \times 100$$

[Molecular Weight of Hyaluronic Acid Derivative (A)]

Although the molecular weight of the hyaluronic acid derivative (A) is not particularly limited, the hyaluronic acid derivative (A) preferably has a relatively large molecular weight from the viewpoint of an expectation of a sustained-release function due to diffusion delay by local administration and the precipitation forming ability under a physiological saline concentration, whilst preferably has a relatively small molecular weight from the viewpoint of syringeability in a case where the final dosage form is a solution formulation. Such a molecular weight of the hyaluronic acid derivative (A) is preferably 1,000 (1 kDa) to less than 1,000,000 (1,000 kDa), more preferably 3 kDa to 500 kDa, even more preferably 5 kDa to 300 kDa, even more preferably 5 kDa to 120 kDa, and particularly preferably 10 kDa to 100 kDa. The molecular weight of the hyaluronic acid derivative (A) can be generally controlled by using a raw material having a corresponding molecular weight.

The term "molecular weight of the hyaluronic acid derivative (A)" used herein is a weight-average molecular weight determined by size exclusion chromatography with a multiangle light scattering detector (SEC-MALS). Specifically, the molecular weight may be measured by the method described in below examples.

Preferable examples of the hyaluronic acid derivative (A) include hyaluronic acid derivatives having at least one repeating unit of the following general formula (I) (hereinafter, may be referred to as "repeating unit (I)").

In the formula, $R^1$, $R^2$, $R^3$, and $R^4$ are each independently selected from the group consisting of a hydrogen atom, $C_{1-6}$ alkyls, a formyl and $C_{1-6}$ alkylcarbonyls;

Z is a direct bond or a peptide linker composed of 2 to 30 arbitrary amino acid residues;

$X^1$ is a group selected from groups of the following formulae:

—$NR^b$—R,
—$NR^b$—COO—R,
—$NR^b$—CO—R,
—$NR^b$—CO—$NR^c$—R,
—COO—R,
—O—COO—R,
—S—R,
—CO—$Y^a$—S—R,
—O—CO—$Y^b$—S—R,
—$NR^b$—CO—$Y^b$—S—R, and
—S—S—R, wherein $R^a$, $R^b$ and $R^c$ are each independently selected from the group consisting of a hydrogen atom, $C_{1-20}$ alkyls, amino $C_{2-20}$ alkyls and hydroxy $C_{2-20}$ alkyls, wherein a group selected from the group consisting of —O— and —$NR^f$— may be inserted in an alkyl moiety thereof;

$R^f$ is selected from the group consisting of a hydrogen atom, $C_{1-12}$ alkyls, amino $C_{2-12}$ alkyls and hydroxyl $C_{2-12}$ alkyls, wherein a group selected from the group consisting of —O— and —NH— may be inserted in an alkyl moiety thereof;

R is a steryl group;

Y is a $C_{2-30}$ alkylene, or —$(CH_2CH_2O)_m$—$CH_2CH_2$—, and a group selected from the group consisting of —O—, —$NR^a$— and —S—S— may be inserted in the alkylene;

$R^g$ is selected from the group consisting of a hydrogen atom, $C_{1-20}$ alkyls, amino $C_{2-20}$ alkyls and hydroxy $C_{2-20}$ alkyls, wherein a group selected from the group consisting of —O— and —NH— may be inserted in an alkyl moiety thereof;

$Y^a$ is a $C_{1-5}$ alkylene;

$Y^b$ is a $C_{2-8}$ alkylene or a $C_{2-8}$ alkenylen; and m is an integer of 1 to 100.

The hyaluronic acid derivative (A) preferably contains a hyaluronic acid derivative having at least one repeating unit of the following general formula (Ia) (hereinafter, may be referred to as "repeating unit (Ia)").

In the formula, $R^1$, $R^2$, $R^3$, and $R^4$ are each independently selected from the group consisting of a hydrogen atom, $C_{1-6}$ alkyls, a formyl and $C_{1-6}$ alkylcarbonyls;

X is a hydrophobic group of —$NR^a$—Y—$NR^b$—COO—R;

$R^a$ and $R^b$ are each independently selected from the group consisting of a hydrogen atom and $C_{1-6}$ alkyls;

R is a steryl group;

Y is a $C_{2-30}$ alkylene or —$(CH_2CH_2O)_m$—$CH_2CH_2$—, and m is an integer of 1 to 100.

In a case where the hyaluronic acid derivative (A) has at least two repeating units (I) or (Ia) respectively, the repeating units may be identical to or different from each other.

The hyaluronic acid derivative (A) may be modified at a position other than the repeating unit (I) or the repeating unit (Ia). For example, a hydroxy group may be converted into —$O(C_{1-6}$ alkyl), —O(formyl), —$O(C_{1-6}$ alkylcarbonyl), or the like, and a carboxy group may be converted into an amide or an ester or may form a salt.

[Repeating Unit (I)]

In the general formula (I), the group of "—Z—$N(R^a)Y$—$X^1$" is preferably a group selected from groups of the following formulae:

NH—$(CH_2)_{mz}$—NH—R;
NH—$(CH_2)_{mz}$—COO—R;
NH—$(CH_2CH_2O)_m$—$CH_2CH_2$—COO—R,
—NH—$(CH_2)_{mz}$—O—COO—R;
—NH—$(CH_2CH_2O)_m$—$CH_2CH_2$—O—COO—R,
—NH—$(CH_2)_{mz}$—S—R;
—NH—$(CH_2CH_2O)_m$—$CH_2CH_2$—S—R;
NH—$(CH_2)_{mz}$—O—CO—CH($R^8$)—$CH_2$—S—R;
NH—$(CH_2)_{mz}$—NHCO—CH($R^8$)—$CH_2$—S—R;
NH—$(CH_2CH_2O)_m$—$CH_2CH_2$—NHCO—CH($R^8$)—$CH_2$—S—R;
—NH—$(CH_2CH_2O)_m$—$CH_2CH_2$—O—CO—CH($R^8$)—$CH_2$—S—R;
—NH—$(CH_2)_{mz}$—S—S—R; and
—Z—$NR^a$—Y—$NR^b$—COO—R, (in the formula, mz is an integer of 2 to 30, $R^8$ is a hydrogen atom or a methyl group, and Z, $R^a$, Y, $R^b$, R and m are defined above in the present specification).

The group: —Z—$NR^a$—Y—$NR^b$—COO—R is preferably a group selected from groups of the following formulae:

—NH—$(CH_2)_{mz}$—NH—COO—R; and

—NH—$(CH_2CH_2O)_m$—$CH_2CH_2$—NH—COO—R, (in the formulae, R, mz and m are defined above in the present specification).

Among these, the group "—Z—N($R^a$)Y—$X^1$" in the general formula (I) is more preferably a group selected from the group consisting of:

NH—$(CH_2)_{mz}$—NH—COO—R;

NH—$(CH_2CH_2O)_m$—$CH_2CH_2$—NH—COO—R; and

NH—$(CH_2)_{mz}$—S—S—R, (in the formulae, mz, R, and m are defined above in the present specification).

(Z)

In the general formula (I), Z is preferably a direct bond.

When Z is a peptide linker in another aspect, $X^1$ is preferably —$NR^b$—COO—R.

In another aspect, Z may be a peptide linker of —NH—[CH(—$Z^a$)—CONH]$_{n-1}$—CH(—$Z^a$)—CO—, in which n is an integer of 2 to 30, and $Z^a$ is each independently a substituent in an α-amino acid of $H_2N$—CH(—$Z^a$)—COOH. The peptide linker binds to a carboxy group of a glucuronic acid moiety at the N terminal, and binds to the group of —N(—$R^a$)—Y—$X^1$ at the C terminal. Examples of an amino acid that is available as an amino acid residue of the peptide linker include α-amino acids such as natural type (L type) amino acids such as alanine, arginine, asparagine (Asn), aspartic acid, cysteine, glutamine, glutamic acid, glycin (Gly), histidine, isoleucine, leucine (Leu), lysine, methionine, phenylalanine (Phe), proline, serine, threonine, tryptophan, tyrosine, and valine, and D-forms thereof. Any α-amino acid, including synthesized amino acids, may be used. Specific examples of $Z^a$ include —$CH_3$, $H_2NC(NH)$NH$(CH_2)_3$—, and $H_2NCOCH_2$—. In addition, n-Z may be identical to or different from each other. Although n is an integer of 2 to 30, n is preferably 2 to 10, and more preferably 2 to 4. Examples of a preferred peptide linker include -Gly-Phe-Leu-Gly-, -Asn-Phe-Phe-, -Phe-Phe-, and Phe-Gly-.

(Y)

In the general formula (I), Y is preferably a group selected from the group consisting of —$(CH_2)_{nt}$— and $(CH_2CH_2O)_{m1}$—$CH_2CH_2$— (wherein n1 is an integer of 2 to 20, preferably an integer of 2 to 15, more preferably an integer of 2 to 12, and even more preferably an integer of 2 to 6; and m1 is an integer of 1 to 4), and specifically preferably —$(CH_2)_2$—, —$(CH_2)_6$—, —$(CH_2)_8$—, —$(CH_2)_{12}$—, or, —$(CH_2CH_2O)_2$—$CH_2CH_2$—. In addition, Y is preferably a group selected from the group consisting of —$(CH_2)_2$—, —$(CH_2)_6$—, —$(CH_2)_8$— and —$(CH_2)_{12}$—, and more preferably —$(CH_2)_6$—, from the viewpoint of realization of high precipitation forming ability under a physiological saline concentration while realizing high solubility in pure water or under a low salt concentration.

For example, Y may be —$CH_2CH_2O$—$CH_2CH_2$—S—S—$CH_2CH_2O$—$CH_2CH_2$—, —$(CH_2CH_2O)_2$—$CH_2CH_2$—S—S—$CH_2CH_2O$—$CH_2CH_2$—, —$CH_2CH_2O$—$CH_2CH_2$—S—S—$(CH_2CH_2O)_2$—$CH_2CH_2$—, —$(CH_2CH_2O)_2$—$CH_2CH_2$—S—S—$(CH_2CH_2O)_2$—$CH_2CH_2$—, or the like.

($Y^a$)

$Y^a$ is preferably —$CH_2$— or —$CH_2$—$CH_2$—.

($Y^b$)

$Y^b$ is preferably —$CH_2$—$CH_2$—, —$CH(CH_3)CH_2$—, 2-butene-1,4-diyl, hepta-2,4-diene-1,6-diyl or octa-2,4,6-triene-1,8-diyl, and more preferably —$CH_2$—$CH_2$— or —$CH(CH_3)CH_2$—.

(R)

R is preferably a cholesteryl group.

Specific examples of the group "—Z—N($R^a$)Y—$X^1$" include —NH—$(CH_2)_2$—NH—CO-cholesteryl, —NH—$(CH_2)_4$—NH—$(CH_2)_3$—NH—$(CH_2)_3$—NH—COO-cholesteryl, —NH—$(CH_2)_3$—NH—$(CH_2)_4$—NH—$(CH_2)_3$—NH—COO-cholesteryl, —NH—$(CH_2)_4$—NH—$(CH_2)_3$—NH—COO-cholesteryl, —NH—$(CH_2)_4$—N(—$(CH_2)_3$—$NH_2$)—COO-cholesteryl, —NH—$(CH_2)_3$—NH—$(CH_2)_4$—N(—$(CH_2)_3$—$NH_2$)—COO-cholesteryl, —NH—$(CH_2)_3$—NH—$(CH_2)_4$—N(—$(CH_2)_3$—NH—$(CH_2)_3$—$NH_2$)—COO-cholesteryl, —NH—$(CH_2)_3$—NH—$(CH_2)_4$—N(—$(CH_2)_3$—$NH_2$)—CO—NH-cholesteryl, —NH—$(CH_2)_3$—NH—$(CH_2)_4$—N(—$(CH_2)_3$—$NH_2$)—CO-cholesteryl, or —NH—$(CH_2)_3$—NH—$(CH_2)_4$—N(—$(CH_2)_3$—$NH_2$)—cholesteryl. It is preferable that in the group "—Z—N($R^a$)Y—$X^1$", $R^a$, $R^b$ and $R^c$ be hydrogen atoms, Y be a linear $C_{2-30}$ alkylene or —$(CH_2CH_2O)_m$—$CH_2CH_2$—, and $Y^a$ be a linear $C_{1-5}$ alkylene, or $Y^b$ be a linear $C_{2-8}$ alkylene or a linear $C_{2-8}$ alkenylen.

[Repeating Unit (Ia)]

In the general formula (Ia), X is preferably —NH—$(CH_2)_2$—NH—COO-cholesteryl, —NH—$(CH_2)_6$—NH—COO-cholesteryl, —NH—$(CH_2)_{12}$—NH—COO-cholesteryl or —NH—$(CH_2CH_2O)_2$—$CH_2CH_2$—NH—COO-cholesteryl, and more preferably —NH—$(CH_2)_2$—NH—COO-cholesteryl, —NH—$(CH_2)_6$—NH—COO-cholesteryl or —NH—$(CH_2CH_2O)_2$—$CH_2CH_2$—NH—COO-cholesteryl.

The hyaluronic acid derivative (A) may further include a repeating unit of general formula (II) (hereinafter, may be referred to as "repeating unit (II)") in addition to the repeating unit (I).

(II)

In the formula, $R^{1a}$, $R^{2a}$, $R^{3a}$ and $R^{4a}$ are each independently selected from the group consisting of a hydrogen atom, $C_{1-6}$ alkyls, a formyl and $C_{1-6}$ alkylcarbonyls; and $X^a$ is selected from the group consisting of hydroxy and O-$Q^+$; wherein $Q^+$ is a counter cation.

In a case where the hyaluronic acid derivative (A) has at least two repeating units (II), the repeating units may be identical to or different from each other.

In another aspect, the hyaluronic acid derivative (A) may be a hyaluronic acid derivative substantially composed of the repeating unit (1), the repeating unit (Ia) and the repeating unit (II).

[Repeating Unit (II)]

In the general formula (II), $Q^+$ is not particularly limited, provided that $Q^+$ is a counter cation which forms a salt in water with a carboxy group. In a case of a valency of two or more, $Q^+$ forms salts with a plurality of carboxy groups depending on the valency. Examples of the counter cation include: metal ions such as lithium ion, sodium ion, rubidium ion, cesium ion, magnesium ion, and calcium ion; and ammonium ions of the formula: $N^+$ $R^jR^kR^lR^m$ (in the formula, $R^j$, $R^k$, $R^l$ and $R^m$ are each independently selected from the group consisting of a hydrogen atom and $C_{1-6}$ alkyls). Among these, $Q^+$ is preferably a sodium ion, a potassium ion, or a tetraalkylammonium ion (such as a tetra n-butyl ammonium ion) is preferable. $R^j$, $R^k$, $R^l$ and $R^m$ are preferably the same group as each other, selected from $C_{1-6}$ alkyls, and preferably n-butyl groups.

It is preferable that each of $R^1$, $R^2$, $R^3$, $R^4$, $R^{1a}$, $R^{2a}$, $R^{3a}$ and $R^{4a}$ be a hydrogen atom. In addition, it is preferable that each of $R^a$ and $R^b$ be a hydrogen atom.

Among these, the hyaluronic acid derivative (A) is preferably a hyaluronic acid derivative substantially composed of the repeating unit (I) and repeating unit (II). In the hyaluronic acid derivative (A), for example, 80% or more, preferably 90% or more, more preferably 95% or more, of disaccharide repeating units composed of D-glucuronic acid and N-acetyl-D-glucosamine are the repeating units (1) and (11). The hyaluronic acid derivative may consist of the repeating units (I) and (II).

[Polar Group-Containing Compound (B)]

The polar group-containing compound (B) has at least one functional group selected from the group consisting of a hydroxy group, a carboxy group, an amino group, an amide group, a carbamate group, a urea group and a thiol group.

The amount of the polar group-containing compound (B) relative to the mass of the hyaluronic acid derivative (A) is preferably 0.001 ppm by mass to less than 1000 ppm by mass, more preferably 0.001 ppm by mass to 900 ppm by mass, even more preferably 0.005 ppm by mass to 800 ppm by mass, and particularly preferably 0.006 ppm by mass to 700 ppm by mass.

When the amount of the polar group-containing compound (B) is the above-mentioned lower limit or more, the precipitation forming ability of the hyaluronic acid derivative composition under a physiological saline concentration can be further improved. In contrast, when the amount of the polar group-containing compound (B) is the above-mentioned upper limit or less, an aggregation of the hyaluronic acid derivative (A) in pure water or under a low salt concentration can be suppressed further effectively, thereby further improving a filterability of an aqueous solution of the hyaluronic acid derivative composition when subjected to sterile filtration using a 0.22 μm filter.

The amount of the polar group-containing compound (B) may be measured by a gas chromatography—mass spectroscopy (GC-MS) method, and specifically may be measured by the method described in below examples.

As the polar group-containing compound (B), a compound having at least one hydroxy group is preferably contained, and alcohol is preferably contained. The alcohol serves as an aggregation promoter of the hyaluronic acid derivative (A) under a physiological saline concentration, and improves the precipitation forming ability of the hyaluronic acid derivative (A) under a physiological saline concentration. Alcohols are predominantly water-soluble compounds and compatible with a steryl skeleton, and sterol compounds exhibit a relatively high solubility therein. Therefore, when the hyaluronic acid derivative (A) is dispersed in water, nano-order gels are spontaneously formed, but it is thought that the presence of the alcohol tends to enhance the fluidity of the cholesterol domain and facilitate physical crosslinking between nano-order gels. Accordingly, it is thought that the presence of trace amounts of alcohol facilitates aggregation between nanogels and improves the precipitation forming ability under a physiological saline concentration.

The alcohol may be monoalcohol or polyhydric alcohol. Examples of the monoalcohol include methanol, ethanol, 1-propanol, 2-propanol (isopropanol), 1-butanol, 2-butanol, isobutanol, 1-pentanol, 2-pentanol, isoamyl alcohol, 1-hexanol, 2-hexanol, 1-heptanol, 1-octanol, 2-ethyl-1-hexanol, 3,3,5-trimethyl-1-hexanol, tridecanol, pentadecanol, palmityl alcohol, stearyl alcohol, cyclopentanol, cyclohexanol, methylcyclohexanol, and trimethylcyclohexanol. The polyhydric alcohol may be divalent alcohol or trivalent alcohol. Examples of the divalent alcohol include ethylene glycol, diethylene glycol, propylene glycol, dipropylene glycol, neopentyl glycol, 1,4-butanediol, and 1,6-hexanediol. Examples of the trivalent alcohol include glycerine and trimethylolpropane.

Among them, the alcohol is preferably at least one alcohol selected from the group consisting of ethanol, isopropanol and polyhydric alcohol, more preferably polyhydric alcohol, and even more preferably ethylene glycol.

The polar group-containing compound (B) is preferably a polyfunctional compound having a plurality of polar groups. In this case, hydrogen bonding between hyaluronic acids, specifically hydrogen bonding between the nano-order gels, is promoted, thereby tending to make it easier to form aggregation, and improving the precipitation forming ability under a physiological saline concentration.

As the polar group-containing compound (B) having a carboxy group, a $C_{1-12}$ branchable hydrocarbonic acids such as formic acid, acetic acid, propionic acid, butyric acid, valeric acid, or hexanoic acid; or a carboxylic acid compound having an aromatic group such as benzoic acid can be mentioned. As a polyfunctional carboxylic acid compound, oxalic acid, malonic acid, succinic acid, glutaric acid, adipic acid, pimelic acid, suberic acid, azelaic acid, sebacic acid, phthalic acid, isophthalic acid, or terephthalic acid can be mentioned. The polyfunctional carboxylic acid compound is preferably contained from the viewpoint of promoting aggregation. A compound having both a carboxy group and a hydroxy group, such as salicylic acid, is preferable from the viewpoint of the presence of a plurality of hydrogen-bondable functional groups.

As the polar group-containing compound (B) having an amino group, a primary, secondary, or tertiary amine compound can be used from the viewpoint of interacting with a carboxy of the hyaluronic acid derivative (A), and a quaternary ammonium salt can be used by salt exchange.

As the amine compound, a primary to tertiary amine compound having a $C_{1-12}$ branchable hydrocarbon group, such as methylamine, ethylamine, n-propylamine, butylamine, dimethylamine, diethylamine, di-n-propylamine, trimethylamine, triethylamine, or tri-n-propylamine; or a quaternary ammonium salt having a $C_{1-12}$ branchable hydrocarbon group, such as tetramethylammonium fluoride, tetramethylammonium chloride, tetramethylammonium bromide, tetramethylammonium iodide, tetraethylammonium fluoride, tetraethylammonium chloride, tetraethylammonium bromide, tetraethylammonium iodide, tetra-n-propyl fluoride, tetra-n-propyl chloride, tetra-n-propyl bromide, tetra-n-propyl iodide, tetra-n-butyl fluoride, tetra-n-butyl chloride, tetra-n-butyl bromide, or tetra-n-butyl iodide can be mentioned.

As the polar group-containing compound (B) having an amide group, a condensation compound of a $C_{1-12}$ branchable hydrocarbonic acid and a primary or secondary amine compound having a $C_{1-12}$ branchable hydrocarbon group can be mentioned. For example, N,N-dimethylformamide or N,N-dimethylacetamide can be mentioned. In addition, a cyclic amide compound such as β-lactam, γ-lactam, or δ-lactam may be used.

As the polar group-containing compound (B) having a thiol, a compound having a $C_{1-12}$ branchable hydrocarbon group, such as methanethiol, ethanethiol, or n-propylthiol can be mentioned.

In addition, a compound having a urea group such as urea or a compound having a carbamate group may also be used as the polar group-containing compound (B).

<Preparation Method of the Hyaluronic Acid Derivative Composition>

The hyaluronic acid derivative composition according to the present embodiment can be prepared by preparing the hyaluronic acid derivative (A), followed by adding the polar group-containing compound (B) having at least one functional group selected from the group consisting of a hydroxy group, a carboxy group, an amino group, an amide group, a carbamate group, a urea group and a thiol group to the hyaluronic acid derivative (A).

As the preparation method of the hyaluronic acid derivative (A), for example, a carboxy group of a glucuronic acid is converted to an amide, and then a steryl group is introduced thereinto to obtain the hyaluronic acid derivative (A). In addition, the introduction ratio of steryl group can be made within a range of 0.1% to less than 35% by controlling the formulation amount of a compound having a steryl group to be reacted, relative to a raw material hyaluronic acid or a derivative thereof.

As the method of converting a carboxy group of a glucuronic acid to an amide and then introducing a steryl group, specifically for example, a method in which a raw material hyaluronic acid or a derivative thereof, preferably a hyaluronic acid consisting of repeating units (II) or a derivative thereof, is ion-exchanged to a tetraalkylammonium salt (such as tetrabutylammonium (TBA) salt), followed by reacting the resultant hyaluronic acid salt with an amine having an introduced steryl group (particularly, cholesteryl group) of the formula: "$HNR^a$—Y—$NR^b$—R, $NHR^a$—Y—$NR^b$—COO—R, $HNR^a$—Y—$NR^b$—COO—R, $HNR^a$—Y—$NR^b$—CO—R, $HNR^a$—Y—$NR^b$—CO—$NR^c$—R, $HNR^a$—Y—COO—R, $HNR^a$—Y—O—COO—R, $HNR^a$—Y—S—R, $HNR^a$—Y—CO—$Y^a$—S—R, $HNR^a$—Y—O—CO—$Y^b$—S—R, $HNR^a$—Y—$NR^b$—CO—$Y^b$—S—R, $HNR^a$—Y—S—S—R, or Z—$NR^a$—Y—$NR^b$—COO—R (in the formula, $R^a$, $R^b$, $R^c$, Y, $Y^a$, $Y^b$, Z and R are defined above in the present specification)" in the presence of an appropriate condensation agent in a solven, can be mentioned.

The condensation agent available in the reaction is not particularly limited, and examples thereof include 4-(4,6-dimethoxy-1,3,5-triazine)-4-methylmorpholinium (DMT-MM), N,N'-carbonyldiimidazole (CDI), N,N'-dicyclohexyl-carbodiimide (DCC), N-ethoxycarbonyl-2-ethoxy-1,2-dihydroquinoline (EEDQ), 2-benzotriazole-1,1,3,3-tetramethyluronium tetrafluoroborate (TBTU), 3,4-dihydro-3-hydroxy-4-oxo-1,2,3-benzotriazine (HODhbt), benzotriazol-1-oxy-tris-pyrrolidino-phosphonium hexafluorophosphate (PyBOP), benzotriazol-1-yl-oxy-tris(dimethyl-amino)phosphonium hexafluorophosphate (BOP), 1-ethyl-3-(3-dimethylaminopropyl)carbodiimide (EDC), and N-hydroxysuccinimide (NHS).

Although there is no particular limitation, DMT-MM is preferable in that the reaction proceeds with high efficiency even in a mixed solvent of water and an organic solvent. In addition, the use of DMT-MM as a condensation agent makes it possible to highly selectively form an amide bond by an amino group and a carboxy group while suppressing the formation of an ester bond in a system in which a large number of hydroxys coexist. The use of the condensation agent makes it possible, for example, to prevent an alcohol as a solvent from reacting with a carboxy group of a hyaluronic acid moiety or prevent a carboxy group and a hydroxy that are simultaneously present in a hyaluronic acid moiety from bonding intramolecularly or intermolecularly, thereby forming undesired crosslinks.

Examples of the solvent used in the steryl group introduction reaction include water, DMSO, methanol, ethanol, propanol, butanol, isopropanol, polyhydric alcohol, acetonitrile, DMF, THF, dichloromethane, chloroform, hexane, diethyl ether, ethyl acetate, and mixture solvents thereof. Examples of the polyhydric alcohol include those exemplified as the above-mentioned alcohols.

Alternatively, a raw material hyaluronic acid or a derivative thereof may be ion-exchanged to a tetraalkylammonium salt (such as a tetrabutylammonium (TBA) salt), followed by reacting the hyaluronic acid salt and a spacer moiety in a solvent in the presence of a suitable condensation agent (at this time, protection and deprotection reactions may be carried out, if necessary), converting a carboxy group (—COOH) of the raw material hyaluronic acid or the derivative thereof, and then reacting the resultant with an appropriate reagent. Examples of a combination of a group derived from the carboxy group and the reaction reagent are shown below:

$CONR^a$—Y—$NR^b$H+Hal-R;
$CONR^a$—Y—$NR^b$H+Hal-COOR;
$CONR^a$—Y—$NR^b$H+HOCO—R;
$CONR^a$—Y—$NR^b$H+Hal-CO—R;
$CONR^a$—Y—$NR^b$—COOH+$HNR^c$—R;
$CONR^a$—Y—$NR^b$—CO—$NR^c$H+Hal-R;
$CONR^a$—Y—$NR^b$H+HOCO—$NR^c$—R;
$CONR^a$—Y—$NR^b$H+Hal-CO—$NR^c$—R;
$CONR^a$—Y—COOH+HO—R;
$CONR^a$—Y—OH+Hal-COO—R;
$CONR^a$—Y—OCOOH+HO—R;
$CONR^a$—Y—OCOOH+Hal-R;
$CONR^a$—Y—OCO-Hal+HO—R;
$CONR^a$—Y—SH+Hal-R;
$CONR^a$—Y-Hal+HS—R;
$CONR^a$—Y—CO—$Y^a$-Hal+HS—R;
$CONR^a$—Y—CO—$Y^a$—SH+Hal-R;
$CONR^a$—Y—O—CO—CH=$CH_2$+HS—R;
$CONR^a$—Y—$NR^b$—CO—CH($CH_3$)=$CH_2$+HS—R;
$CONR^a$—Y—SH+HS—R;
COZ—OH+$HNR^a$—Y—$NR^b$—COO—R; and
COZ—$NR^a$—Y—$NR^b$H+Hal-COO—R,
(in the formulae, $R^a$, $R^b$, $R^c$, Y, $Y^a$ $Y^b$, and Z are defined above in the present specification, and Hal is a halogen atom selected from the group consisting of a fluorine atom, a chlorine atom, a bromine atom and an iodine).

Examples of the reaction mode include dehydrohalogenation reaction, condensation reaction, dehydration reaction, nucleophilic addition reaction such as Michael addition, and oxidative disulfide formation reaction, which are well-known reactions and are appropriately selected by those skilled in the art to be carried out while finding favorable reaction conditions. In a case where a transformant or a reactant has a carboxy group, it may be made into an N-hydroxysuccinimide (hereinafter, may also be referred to as "NHS") ester and then subjected to reaction.

Furthermore, a method in which a 2-aminoethyl 2-pyridyl disulfide is reacted with a carboxy group of the raw material hyaluronic acid or the derivative thereof to prepare a hyaluronic acid derivative in which a spacer having a mercapto group modified with a leaving group at the terminal thereof is introduced, followed by subjecting the resultant to a nucleophilic substitution reaction with a thiocholesterol to form a disulfide bond can be mentioned.

Furthermore, a method in which a hyaluronic acid or a derivative thereof in which a part of spacer is introduced into a carboxy group and a steryl group in which a part of spacer is introduced are prepared and reacted can also be mentioned. Although some specific examples have been described above, in a case where —S—S— is inserted in Y, a hyaluronic acid derivative in which a spacer having a mercapto group at the terminal thereof is introduced into a carboxy group of a hyaluronic acid, and a steryl group into which a spacer having a mercapto group at the terminal thereof is introduced are prepared and reacted oxidatively to form a disulfide bond. At this time, one mercapto group may be reacted with 2-mercaptopyridine to form a disulfide, followed by substituting with the other mercapto group.

Furthermore, after preparing the hyaluronic acid derivative according to the present invention, another substituent may be introduced. For example, 0.1% to 99.5%, and preferably 10% to 40% of carboxy groups in the hyaluronic acid derivative substantially composed of the repeating unit (1) and the repeating unit (II) may be substituted with —CO—V, (wherein, $X^z$ is selected from the group consisting of the following groups:

—NH—$(CH_2)_{p1}$—O—CO—C$(R^{17})$=$CH_2$;

—NH—$(CH_2)_{p1}$—O—CO—CH$(R^{17})$—$CH_2$—S— $CH_2$—CH(OH)—CH(OH)—$CH_2$—SH;

—NH—$(CH_2)_{p1}$—SH;

—NH—$(CH_2)_{p1}$—NH—CO—C$(R^{17})$=$CH_2$;

—NH—$(CH_2)_{p1}$—NH—C(=NH)—$(CH_2)_3$—SH;

—NH—$(CH_2)_{p1}$—NH—CO—$(CH_2)_r$—SH;

—NH—$(CH_2)_{p1}$—NH—CO—CH$(R^{17})$—$CH_2$—S— $CH_2$—CH(OH)—CH(OH)—$CH_2$—SH;

—NH—$(CH_2)_{p1}$—NH—CO—CH$(NH_2)$—$CH_2$—SH;

—NH—$(CH_2)_p$i-NH—CO—CH$(NH_2)$—$(CH_2)_2$—SH;

—NH—NH—CO—$(CH_2)_4$—CO—NH—NH—C (=NH)—$(CH_2)_3$—SH;

—NH—$(CH_2$—$CH_2$—O$)_q$—$CH_2$—$CH_2$—O—CO—C $(R^{17})$=$CH_2$;

—NH—$(CH_2$—$CH_2$—O$)_q$—$CH_2$—$CH_2$—O—CO—CH $(R^{17})$—$CH_2$—S—$CH_2$—CH(OH)—CH(OH)—$CH_2$— SH;

—NH—$(CH_2$—$CH_2$—O$)_q$—$CH_2$—$CH_2$—SH;

—NH—$(CH_2$—$CH_2$—O$)_q$—$CH_2$—$CH_2$—NH—CO—C $(R^{17})$=$CH_2$;

—NH—$(CH_2$—$CH_2$—O$)_q$—$CH_2$—$CH_2$—NH—C (=NH)—$(CH_2)_3$—SH;

—NH—$(CH_2$—$CH_2$—O$)_q$—$CH_2$—$CH_2$—NH—CO— $(CH_2)_2$—SH;

—NH—$(CH_2$—$CH_2$—0$)_q$—$CH_2$—$CH_2$—NH—CO— CH$(R^{17})$—$CH_2$—S—$CH_2$—CH(OH)—CH(OH)— $CH_2$—SH;

—NH—$(CH_2$—$CH_2$—O$)_q$—$CH_2$—$CH_2$—NH—CO— CH$(NH_2)$—$CH_2$—SH;

—NH—$(CH_2$—$CH_2$—O$)_q$—$CH_2$—$CH_2$—NH—CO— CH$(NH_2)$—$(CH_2)_2$—SH;

—NH—CH$(CO_2H)$—$(CH_2)$—SH;

—NH—CH$(CO_2H)$—$(CH_2)_2$—SH; and

—NH—CH$(CO_2H)$—$(CH_2)_2$—CONH—CH(CONH— $CH_2$—$CO_2H)$—$CH_2$—SH, (wherein $R^{17}$ is a hydrogen atom or a $C_{1-6}$ alkyl group, p1 is an integer of 2 to 10, q is an integer of 1 to 200, and r is an integer of 1 to 3)], to form a cross-link to cause gelation in a molecule or between molecules including other molecules.

The conditions under which the hyaluronic acid derivative (A) is allowed to gelate by chemical cross-linking may be appropriately selected. The cross-linking conditions include a cross-linking method, a polymer concentration, a cross-linking agent concentration, a solvent, a solvent pH, a salt concentration, a temperature, a time and the like.

Among the reaction conditions for cross-linking in the step of gelation of the hyaluronic acid derivative, for example, an increase in the polymer concentration at the time of chemical cross-linking and the introduction ratio of cross-linkable groups makes it possible to enhance the crosslinking density of the resultant gel.

In a case where a compound that can form cross-links at both ends is used in the step of gelation of the hyaluronic acid derivative (A), the cross-linking agent is preferably added at a concentration which allows the groups to quickly participate in the cross-linking reaction without excess or deficiency. For example, when a polymer into which a methacryloyl group (MA group) is introduced is crosslinked by a Michael addition reaction using DTT, the ratio MA group:SH group is preferably 3:1 to 1:3, and particularly preferably 2:1 to 1:2.

The solvent in the step of gelation of the hyaluronic acid derivative (A) is preferably a solvent in which a polymer and a cross-linking agent can be sufficiently dissolved, and is not particularly limited, but is preferably water, dimethyl sulfoxide (DMSO), dimethylacetamide (DMAc), dimethylformamide (DMF), N-methylpyrrolidone (NMP) or a mixed solvent selected therefrom. An organic solvent miscible with these solvents may also be mixed to be used. Although there is no particular limitation, examples of the miscible organic solvent include methanol, ethanol, propanol, isopropanol, butanol, polyhydric alcohol, acetone, and acetonitrile. Examples of the polyhydric alcohol include those similar to those exemplified as the above-mentioned "alcohol", and among them, ethylene glycol is preferable.

Since the hyaluronic acid derivative (A) forms nanoparticles in an aqueous solution, nano-sized fine particle gels can be formed by cross-linking under dilute conditions, and the hyaluronic acid derivative (A) may be used as a sustained-release carrier in the blood or a targeting carrier. The dilute conditions mean 10 mg/mL or less, preferably 5 mg/mL or less, and more preferably 1 mg/mL or less. On the other hand, it is possible to form a bulk gel in which fine particles are cross-linked with each other by cross-linking under high concentration conditions. This is useful as a subcutaneous sustained-release carrier. The high concentration conditions mean 5 mg/mL or more, preferably 20 mg/mL or more, and more preferably 40 mg/mL.

The step of gelation of the hyaluronic acid derivative (A) may be carried out in bulk or in a discontinuous phase such as in an emulsion or spray droplets. For example, when the step is carried out in a W/O emulsion, an aqueous phase in which a polymer, a cross-linking agent or the like is dissolved may be emulsified in a solvent immiscible with water, followed by allowing a gelation reaction to proceed. Although the solvent immiscible with water is not particularly limited, examples thereof include hexane, chloroform, dichloromethane, ethyl acetate, medium chain fatty acid triglyceride (MCT), liquid paraffin, and soybean oil. A surfactant which contributes to stabilization of emulsification may be added. Alternatively, for example, the step may be carried out in a solvent capable of desolventizing, such as supercritical carbon dioxide or PEG. In this case, an aqueous phase or an organic solvent phase in which a polymer or a cross-linking agent is dissolved is emulsified and dispersed in the above-mentioned solvent to cause condensation of the polymer due to desolventizing (solvent diffusion), thereby making it possible to obtain a gel having a higher crosslink density.

After the step of gelation of the hyaluronic acid derivative (A), an operation of stopping the cross-linking reaction and an operation of deactivating or washing the remaining cross-linkable functional group may be performed. Cross-linkable functional groups that do not participate in the reaction, groups to which only one end of the crosslinking agent is bonded, remaining crosslinking agents, or the like, are preferably removed from the viewpoint of safety, stability during storage, side reactions with an encapsulated drug, or the like. Although there is no particular limitation, when an unreacted cross-linking agent remains, for example, it may be removed by washing with excess water or the like. Furthermore, for example, when a methacryloyl group substituted with a polymer remains, it may be removed by adding excess mercaptoethanol or the like to inactivate the methacryloyl group and then washing the redundant mercaptoethanol with excess water or the like. Furthermore, for example, when a mercapto group remains, excess 3-maleimide propionic acid, iodoacetic acid, or the like may be added to inactivate the mercapto group, followed by washing the redundant 3-maleimide propionic acid or iodoacetic acid with excess water or the like.

After the step of gelation of the hyaluronic acid derivative (A), a pulverization step may be conducted. Although examples of the pulverization method include pulverization using a pestle and a mortar and pulverization using a mill, pulverization using a mill is preferable. Although examples of mill pulverizers include: rotary disk-type pulverizers such as a centrifugal pulverizer (manufactured by NISSEI Corporation) and an impact mill (manufactured by DALTON CO., LTD.); screen mill pulverizers such as an atomizer (manufactured by TOKYO ATOMIZER M.F.G CO., LTD.), a sample mill (manufactured by TOKYO ATOMIZER M.F.G CO., LTD.), a bantum mill (manufactured by TOKYO ATOMIZER M.F.G CO., LTD.), and an SK mill (manufactured by Tokken, inc.); jet pulverizers such as a super micro labo jet mill (A-O jet mill manufactured by SEISHIN ENTERPRISE CO., LTD.); and a linrex mill (manufactured by Liquid Gas Co., Ltd.) that allows pulverization at a very-low temperature, an SK mill and a linrex mill are preferable.

A drying step may be carried out after the step of gelation of the hyaluronic acid derivative (A). Examples of the drying method include ventilation drying, drying in a thermostat, vacuum drying, and hot air circulating drying. The blowing velocity, drying time, temperature, and pressure are selected as appropriate as long as gel of the hyaluronic acid derivative (A) does not decompose or denature.

In the production of the hyaluronic acid derivative (A), when the polar group-containing compound (B) derived from a solvent used at the time of the production remains, the hyaluronic acid derivative composition may be obtained without adding the polar group-containing compound (B). Alternatively, the hyaluronic acid derivative composition may be obtained by adding the polar group-containing compound (B) after the production of the hyaluronic acid derivative (A) such that the amount of the polar group-containing compound (B) becomes a desired amount. In a case where the polar group-containing compound (B) is added, the polar group-containing compound (B) is preferably added before the drying step.

<<Pharmaceutical Composition>>

A pharmaceutical composition according to the present embodiment contains a drug and a carrier, and contains the above-mentioned hyaluronic acid derivative composition as the carrier. In the pharmaceutical composition according to the present embodiment, the carrier and the drug are directly or indirectly bonded by hydrogen bond, ionic bond, non-covalent bond such as van der Worth force, or the like, to form a complex without being free from each other. When the pharmaceutical composition is administered in vivo, the drug becomes free gradually from the carrier, and favorable sustained-release can be expected.

In the pharmaceutical composition according to the present embodiment, it is preferable that the drug form a complex with the hyaluronic acid derivative (A) as a carrier in the hyaluronic acid derivative composition. It is thought that a steryl group of the hyaluronic acid derivative (A) and a drug present in the system spontaneously associate with each other in a solvent due to hydrophobic interaction therebetween, thereby forming a complex of the drug and the hyaluronic acid derivative (A). The improvement in the storage stability of the drug, the sustention of the biological activity, and the improvement in the sustained release property are expected by forming the complex.

<Drug>

A drug contained in the pharmaceutical composition according to the present invention is not particularly limited, and examples thereof include proteins, peptides, polysaccharides, nucleic acids, and low-molecular-weight compounds. In the pharmaceutical composition according to the present embodiment, a bio-pharmaceutical product such as a pharmacologically active protein, peptide or nucleic acid, or a low-molecular-weight compound is preferably contained while forming a complex with the hyaluronic acid derivative (A) in the hyaluronic acid derivative composition.

[Low-Molecular-Weight Compound]

Examples of the low-molecular-weight compound include carcinostatic agents (such as alkylating agents, antimetabolites, and alkaloids), immunosuppressive agents, anti-inflammatory agents (such as steroid drugs, and non-steroidal anti-inflammatory agents), antirheumatic agents, antibacterial agents (such as β-lactam antibiotics, aminoglycoside antibiotics, macrolide antibiotics, tetracycline antibiotics, new quinolone antibiotics, and sulfa drugs).

[Protein and Peptide]

Examples of protein or peptide include erythropoietin (EPO), granulocyte colony-stimulating factor (G-CSF), interferon-α, β, γ, (INF-α, β, γ), thrombopoietin (TPO), ciliary neurotrophic factor (CNTF), tumor necrosis factor (TNF), tumor necrosis factor binding protein (TNFbp), interleukin-10 (IL-10), FMS-like tyrosine kinase (Flt-3), growth hormone (GH), insulin, insulin-like growth factor-1 (IGF-1), platelet-derived growth factor (PDGF), interleukin-1 receptor antagonist (IL-1ra), brain-derived neurotrophic factor (BDNF), keratinocyte growth factor (KGF), stem cell factor (SCF), megakaryocyte growth and development factor (MGDF), osteoprotegerin (OPG), leptin, parathyroid hormone (PTH), basic fibroblastic growth factor (b-FGF), bone morphogenetic protein (BMP), atrial natriuretic peptide (ANP), brain natriuretic peptide (BNP), C-type natriuretic peptide (CNP), glucagon-like peptide-1 (GLP-1), antibody, diabody, minibody, and fragmented antibody,

[Nucleic Acid]

Examples of nucleic acid include DNA, RNA, antisense nucleic acid, decoy nucleic acid, ribozyme, low-molecular-weight interfering RNA, and nucleic acid aptamer.

[Polysaccharides]

Examples of polysaccharides include lentinan, sizofiran, pachymaran, pustulan, yeast glucan, yeast mannan, marinactan, curdlan, dextran sulfate, heparin, carrageenan, inulin, chondroitin, and chondroitin sulfate.

<Form>

The pharmaceutical composition according to the present embodiment may be a dispersible fine particle solution, a precipitating suspension, or a lyophilized product. In the case of the dispersible fine particle solution, the pharmaceutical composition is in a solution state before administration into the body, whilst may become a precipitation-type sustained-release preparation that has a characteristic of aggregating on the spot in the body after administration by administering it into the body (for example, subcutaneous administration). In the case of the precipitating suspension, the pharmaceutical composition may be a precipitation-type sustained-release preparation characterized in that an active ingredient thereof is less likely to be burst-released. In this case, the size of the precipitate is preferably 200 μm or less, more preferably 100 μm or less, and even more preferably 20 μm or less, since it is possible to impart syringe ability.

Furthermore, in the case of the lyophilized product, the pharmaceutical composition may be a precipitation-type sustained-release preparation which requires preparation of an administration solution by a doctor by adding an isotonic solution such as physiological saline thereto before administration. This case is considered suitable for a pharmaceutical composition containing an active ingredient that is unstable in a solution state.

When the pharmaceutical composition according to the present embodiment is a dispersible fine particle solution or a precipitate suspension, the concentration of the hyaluronic acid derivative (A) in the pharmaceutical composition is preferably 1 mg/mL to 200 mg/mL, more preferably 4 mg/mL to 100 mg/mL, even more preferably 4 mg/mL to 50 mg/mL, and particularly preferably 4 mg/mL to 12 mg/mL. When the concentration of the hyaluronic acid derivative (A) in the pharmaceutical composition is the above-mentioned lower limit or more, the precipitation forming ability under a physiological saline concentration tends to be made more excellent, and the dose of the drug tends to be increased. On the other hand, when the concentration of the hyaluronic acid derivative (A) in the pharmaceutical composition is the above-mentioned upper limit or less, the injectorability when administered into the living body using an injection needle tends to be further improved, and the sterilization filterability tends to be further improved.

<<Hyaluronic Acid Derivative-Drug Conjugate Composition>>

The hyaluronic acid derivative-drug conjugate composition according to the present embodiment contains the hyaluronic acid derivative-drug conjugate composition and one or more drugs, and the one or more drugs are bound to the hyaluronic acid derivative (A) contained in the hyaluronic acid derivative composition.

The drugs suitable to form the hyaluronic acid derivative-drug conjugate composition according to the present embodiment are bio-pharmaceutical products such as proteins, peptides or nucleic acids or low-molecular-weight compounds.

The pharmaceutical composition and hyaluronic acid derivative-drug conjugate composition according to the present embodiment are not limited to be in the form mentioned above, and may be in the form of nanoparticle, microparticle, solution, emulsion, suspension, gel, micelle, implant, powder, or film. The powder may be produced by pulverizing a solid obtained by lyophilization or spray-drying or produced from a dried precipitate.

The pharmaceutical composition and the hyaluronic acid derivative-drug conjugate composition according to the present embodiment may be administered orally, parenterally, intranasally, intravaginally, intraocularly, subcutaneously, intravenously, intramuscularly, intracutaneously, intraperitoneally, intracerebrally or intraorally. The pharmaceutical composition and the hyaluronic acid derivative-drug conjugate composition according to the present embodiment is not limited to an injection, and may be an adhesive skin patch, microneedle preparation, topical cream, ophthalmic preparation, spray or inhalant.

EXAMPLES

Although the present invention will be explained further specifically with reference to examples below, these are not intended to limit the scope of the present invention to the examples.

The measurement method and the evaluation method of each physical property of hyaluronic acid derivative compositions prepared in examples and comparative examples.

[Physical Property 1]

(Molecular Weight of Hyaluronic Acid Derivative)

The molecular weight of the hyaluronic acid derivative is the weight average molecular weight determined by size exclusion chromatography with a multi-angle light scattering detector (SEC-MALS). The hyaluronic acid derivative composition (20 mg) was dissolved in ultrapure water (10 mL) and stirred at room temperature for 12 hours or more to obtain an aqueous solution of the hyaluronic acid derivative composition (2 mg/mL). An aqueous solution of 300 mM hydroxypropyl-β-cyclodextrin (HP-β-CD) (750 μL) was added to the aqueous solution of the hyaluronic acid derivative composition (750 μL), mixed for 10 seconds using a shaker, and incubated at 37° C. for one hour. Then, the obtained sample was subjected to SEC-MALS measurement to determine the weight-average molecular weight. The conditions for SEC-MALS measurement are shown below.

(Measurement Conditions)

Column: Two TSKgel GMPWXL (manufactured by Tosoh Corporation)

Column temperature: 30° C.

Eluent: Phosphate buffered saline containing 10 mM HP-β-CD (pH 7.4)

Flow velocity: 1 mL/min

Injection volume: 200 μL

[Physical Property 2]

(Introduction Ratio of Steryl Group)

The introduction ratio of steryl group in a hyaluronic acid derivative was determined by $^1$H-NMR measurement. First, dimethyl sulfoxide-$d_6$ (99.9 v/v %, containing 0.05 v/v % trimethylsilyl (TMS), manufactured by Fujifilm Wako Pure Chemical Corporation) and 20% deuterium chloride (99.5 v/v %, manufactured by Fujifilm Wako Pure Chemical Corporation) were mixed at a mass ratio of 99:1 to prepare a measurement solvent. Then, the hyaluronic acid derivative composition (2 mg) was added to the measurement solvent (0.6 mL), treated with an ultrasonic bath for 30 minutes to completely dissolve it, and then subjected to $^1$H-NMR measurement. $^1$H-NMR measurement was carried out at a sample temperature of 85° C. using a Fourier transform nuclear magnetic resonance apparatus (FT-NMR apparatus) (ECS400, manufactured by JEOL Ltd.). The introduction ratio of steryl group was calculated from an integral value of a peak derived from acetyl group of N-acetyl-D-glucosamine ($COCH_3$, 1.6 ppm to 2.0 ppm, 3H) and an integral value of a peak derived from methyl group in cholesteryl group ($CH_3$, 0.7 ppm, 3H) as the introduction ratio of the cholesteryl groups to hyaluronic acid units using the equation shown below. Since the peak derived from cholesteryl group (5H) overlapped peaks around 1.6 ppm to 2.0 ppm, which included the peak derived from acetyl group of N-acetyl-D-glucosamine, a value obtained by subtracting $\frac{5}{3}$ of an integrated value of a peak derived from methyl of cholesteryl group (0.7 ppm) from an integrated value of peaks around 1.6 ppm to 2.0 ppm (i.e., integrated value (1.6 ppm to 2.0 ppm)– integrated value (0.7 ppm)×5/3) was used as the integrated value of the peak derived from acetyl group of N-acetyl-D-glucosamine.

[Introduction ratio of steryl group (%)]=[(Integrated value of a peak derived from methyl group of cholesteryl group)/(Integrated value of a peak derived from acetyl group of N-acetyl-D-glucosamine)]×100=[Integrated value(0.7 ppm)/{Integrated value(1.6 ppm to 2.0 ppm)–Integrated value(0.7 ppm)×5/3}]×100

[Physical Property 3]
(Amount of Polar Group-Containing Compound)

The amount of the polar group-containing compound (B) in a hyaluronic acid derivative composition was measured by a gas chromatography-mass spectrometry (GC-MS) method.

First, the hyaluronic acid derivative composition (16.0 mg) was added to ultrapure water (2.0 mL), and then stirred to be dissolved for 12 hours or more, thereby obtaining an aqueous solution of 8.0 mg/mL of the hyaluronic acid derivative composition. Then, the obtained aqueous solution was subjected to GC-MS measurement, and the amount of the polar group-containing compound (B) in the measurement sample was determined by an external standard method. Then, the mass ratio of the polar group-containing compound (B) in the measurement sample to the amount of the added hyaluronic acid derivative was calculated as the amount of the polar group-containing compound (B) with respect to the hyaluronic acid derivative. The calibration curve required for the quantitative analysis was prepared using a commercially available standard. The conditions for GC-MS measurement are shown below.
(Measurement Conditions)

GC device: Agilent Technologies, 7890A

Column: DB-624 (60 m×0.25 mmΦ), film thickness 1.40 μm

Column temperature: 50° C. (for 5 minutes)→temperature rise at 20° C./min→158° C. (for 2 minutes)→temperature rise at 3° C./min→180° C. (for 0 minutes) →temperature rise at 20° C./min→250° C. (for 5.8 minutes)

Flow velocity: 1 mL/min

Inlet temperature: 250° C.

Split ratio: 1/50

Although it depends on the compound to be quantified, the following method was used in the case of 50 mass ppm or less.
(Measurement Conditions: In the Case of Ethylene Glycol)

0.1 g of a hyaluronic acid derivative was placed in a glass tube, desorbed by heating at 200° C. for 10 minutes, and the volatile components were trapped at –130° C. Then, the cooled trap was rapidly heated at 250° C. and then subjected to GC-MS measurement.

A standard ethylene glycol having a known concentration was measured under the same conditions, and a calibration curve was prepared from the detected peak area value. The mass of ethylene glycol in the sample was calculated from the calibration curve. Then, the mass ratio of ethylene glycol in the sample to the mass of the hyaluronic acid derivative (A) was calculated as the amount of the polar functional group-containing compound (B) relative to the hyaluronic acid derivative (A).

Heat desorption device: GESTEL TDU, CIS4

Desorption temperature: 200° C.

Desorption time: 10 minutes

Split: Splitless

Cryofocusing temperature: –130° C.

Injection temperature: 250° C.

CIS Liner: Tenax (GL Science)

GC device: Agilent Technologies 7890

Column: GL Science DB-WAX (30 m×0.25 mmΦ, film thickness 0.25 mm)

Temperature conditions: 40° C. (for 5 minutes)→20° C./min→250° C. (held for 5 minutes)

MS device: Agilent Technology 7000

Ionization: EI 70 eV

Ion source temperature 250° C.

Scan range: SIM (m/z33)

In the case of isopropanol and ethanol, the measurement was carried out in the same manner as ethylene glycol except that the temperature conditions were as follows: 50° C. (for 5 minutes)→10° C./min→240° C. (held for 6 minutes).
[Evaluation 1]
(Precipitation Ratio)

The precipitation ratio of the hyaluronic acid derivative composition was determined by the following procedure. First, 40 mM phosphate buffer solution (pH 7.4) containing 600 mM sodium chloride was prepared (referred to as a concentrated buffer solution). Next, ultrapure water was added to the hyaluronic acid derivative composition, and the mixture was stirred and dissolved for 12 hours or more to obtain an aqueous solution of the hyaluronic acid derivative composition. The aqueous solution was placed in a filtration tube (pore size: 5.0 μm; UFC40SV25; manufactured by Merck & Co., Inc.), centrifuged, and filtered. Then, precipitate-forming samples (N number: 3) in which the filtered aqueous solution of the hyaluronic acid derivative (600 μL) and a concentrated buffer solution (200 μL) were mixed, and reference samples (N number: 2) in which the filtered aqueous solution of the hyaluronic acid derivative (600 μL) and ultrapure water (200 μL) were mixed were prepared. Then, the precipitate-forming samples and the reference samples were incubated at 37° C. for 20 minutes, and then centrifuged (at 2,000×g for 10 minutes). 200 μL of each supernatant of centrifuged samples was collected, and then diluted 2-fold by adding an aqueous solution of 300 mM hydroxypropyl-β-cyclodextrin (HP-β-CD) (200 μL), followed by incubating at 37° C. for 2 hours. In addition, each of all samples was diluted by adding an aqueous solution of 10 mM HP-β-CD (1000 μL) and treated with a syringe filter (pore size: 0.45 μm). Then, the obtained precipitate-forming samples and reference samples were subjected to size exclusion chromatography (SEC) measurement. The precipitation ratio of the hyaluronic acid derivative composition was calculated in accordance with the following equation using area values of peaks (around 7 minutes) derived from the hyaluronic acid derivative in the SEC chromatogram of the precipitate-forming samples and the reference samples.

[Precipitation rate](%)=[1–(Area value of peak derived from hyaluronic acid derivative in precipitation-forming sample)/(Area value of peak derived from hyaluronic acid derivative in reference sample)]×100

Herein, the average value of area values of the precipitation-forming samples prepared at N=3 was used as the area value of peak derived from hyaluronic acid derivative in precipitation-forming sample, and the average value of area values of the reference samples prepared at N=2 was used as the area value of peak derived from hyaluronic acid derivative in the reference sample. The conditions for SEC measurement are shown below.

(Measurement Conditions)

Column: TSKgel G4000SWXL (manufactured by Tosoh Corporation)

Column temperature: 35° C.

Eluent: Phosphate buffered saline containing 10 mM HP-β-CD (pH 7.4)

Flow velocity: 1 mL/min

Injection volume: 90 μL

Detection: Differential refractive index detector (RI detector) or ultraviolet detector (UV detector)

[Evaluation 2]

(Sterilization Filterability)

The sterilization filterability was evaluated by the maximum amount of filtration when an aqueous solution of the hyaluronic acid derivative composition was treated with a 0.22 μm filter. Namely, the hyaluronic acid derivative composition was dissolved in ultrapure water to 0.9 mg/mL, and the obtained aqueous solution of the hyaluronic acid derivative composition was continuously subjected to filtration through a 0.22 μm filter (Stericup-GP S2GPU05RE, effective filtration area 40 cm², manufactured by Merck & Co., Inc.) until the membrane was clogged and the aqueous solution could not be permeated. Then, the volume of the filtered aqueous solution of the hyaluronic acid derivative composition was measured, and the volume of the filtered aqueous solution of the hyaluronic acid derivative composition per effective filtration area was calculated as the maximum amount of filtration.

<Preparation of Hyaluronic Acid Derivative Composition>

Example 1

(Preparation of Hyaluronic Acid Derivative Composition HA-a1)

A hyaluronic acid derivative composition was prepared by the following steps 1 to 3.

1. Step 1

(Synthesis of Cholesteryl 6-Aminohexylcarbamate Hydrochloride)

Cholesteryl 6-aminohexylcarbamate hydrochloride (Chol hydrochloride) was synthesized by the following Step 1-1 and then Step 1-2.

(1) Step 1-1

To a solution of cholesteryl chloroformate (3.37 g, 7.5 mmol) in anhydride dichloromethane (20 mL), triethylamine (TEA, 1.05 mL) was added in an argon atmosphere and stirred. On ice, 6-(t-butoxycarbonyl)amino-1-aminohexane (1.12 mL, 5 mmol) was added dropwise, and the mixture was stirred for 30 minutes while cooling on ice, and then heated to room temperature, followed by stirring the mixture overnight. The reaction mixture was washed with ultrapure water and with saturated brine and then dried with anhydrous magnesium sulfate, followed by distilling off the solvent under reduced pressure. The resulting residue was purified by silica gel column chromatography (eluent: ethyl acetate:n-hexane=1:4). The fractions of an intended product were combined together, and the solvent was distilled off under reduced pressure.

(2) Step 1-2

The resulting residue was dissolved in ethyl acetate (40 mL), and 4N hydrochloric acid/ethyl acetate solution (40 mL) was added thereto, followed by stirring the mixture overnight at room temperature. The resulting precipitate was collected by centrifugal separation. The resulting solid was washed four times with ethyl acetate and then dried under reduced pressure to obtain 1.2 g of cholesteryl 6-aminohexylcarbamate hydrochloride (Chol hydrochloride). The $^1$H-NMR spectrum of the resultant (CS400 manufactured by JEOL Ltd., EtOH-d$_6$) is shown in FIG. 1.

2. Step 2

(Preparation of Tetrabutylammonium (TBA) Salt of Hyaluronic Acid)

A TBA salt of hyaluronic acid (HA-TBA) was prepared by the following Step 2-1 and then Step 2-2.

(1) Step 2-1

DOWEX (trademark) 50WX-8-400 (manufactured by Aldrich) was suspended in ultrapure water and the resin was washed about three times with ultrapure water by decantation. An aqueous solution of 40% by mass of tetrabutylammonium hydroxide (TBA-OH) (manufactured by Aldrich) was added in an amount of about 1.5-fold molar equivalents relative to the cation exchange capacity of the resin, followed by stirring the mixture for about 30 minutes. After removing the excess of the TBA-OH solution by decantation, the resin was further washed with an excessive amount of ultrapure water to obtain a TBA salt of the cation exchange resin.

(2) Step 2-2

Figure 2:
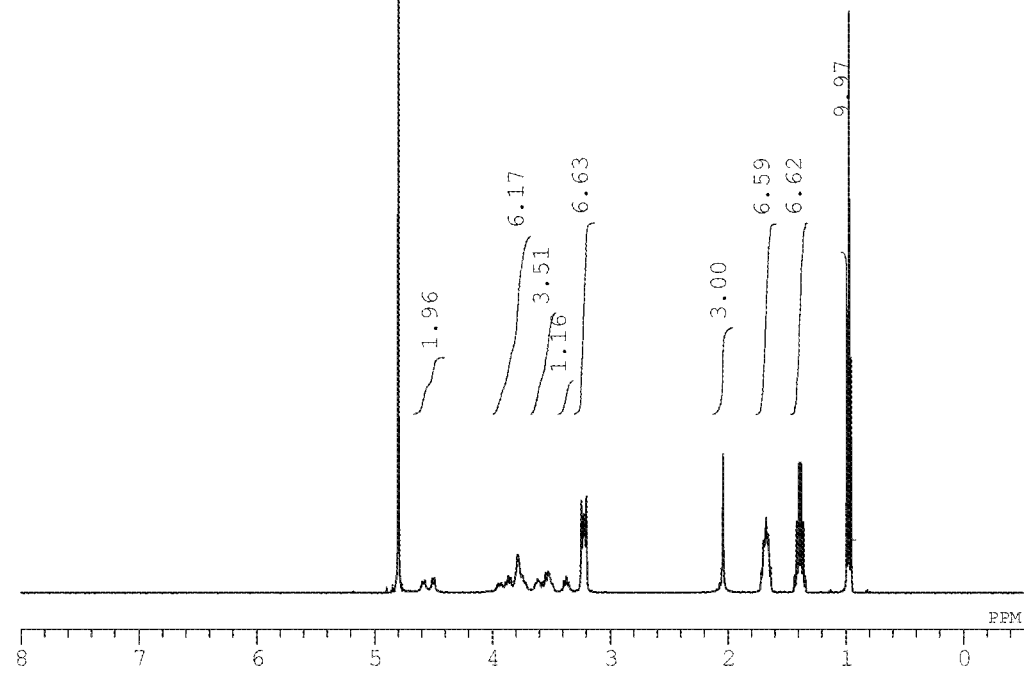
FIG. 2 is $^1$H-NMR spectrum of a tetrabutylammonium (TBA) salt of hyaluronic acid (HA) in Example 1.

A raw material sodium salt of hyaluronic acid (HA-Na) having a molecular weight of 50,000 (50 kDa) was dissolved in ultrapure water at a concentration of 15 mg/mL. A suspension of the TBA salt of the cation exchange resin obtained in the "(1) Step 2-1" was added in an amount of 5-fold molar equivalents relative to HA units (unit molecular weight: 401.3), calculated as the ion exchange capacity of the resin. After stirring the mixture for 15 minutes, filtration was performed with a 0.45 μm filter and the filtrate was lyophilized to obtain a TBA salt of hyaluronic acid (HA-TBA) as a white solid. The $^1$H-NMR spectrum of the resultant (ECS400 manufactured by JEOL Ltd., EtOH-d$_6$) is shown in FIG. 2.

3. Step 3

Figure 3:
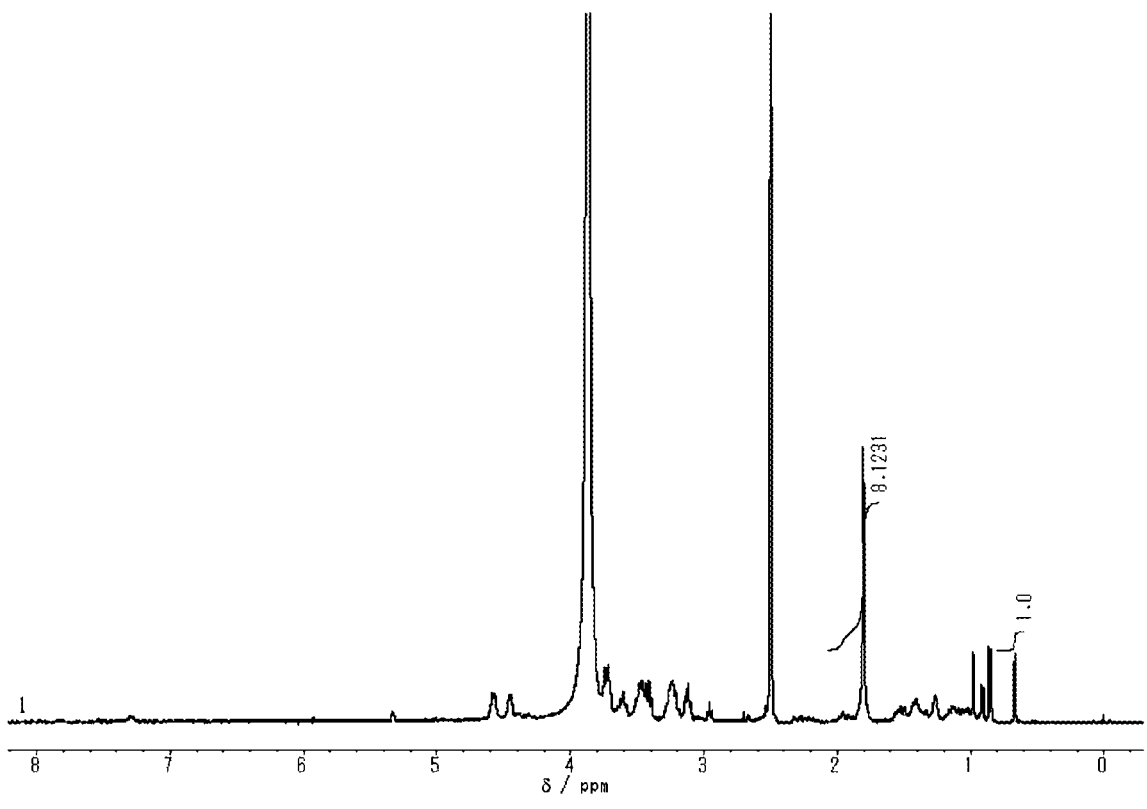
FIG. 3 is $^1$H-NMR spectrum of a HA derivative having an introduced 6-aminohexylcarbamate (HA-$C_6$-Chol) in Example 1.

An anhydrous DMSO solution of the HA-TBA prepared in the "2. (2) Step 2-2" (10 mg/mL) was prepared. Then, the Chol hydrochloride prepared in the "1. Step 1" was added thereto such that the molar ratio thereof relative to disaccharide repeating units (HA units) in the HA-TBA (Chol hydrochloride/HA units) became 15/100. Then, 4-(4,6-dimethoxy-1,3,5-triazin-2-yl)-4-methylmorpholinium chloride (DMT-MM) was added thereto such that the molar ratio thereof relative to HA units (DMT-MM/HA unit) became 21.6/100, followed by stirring the mixture overnight at room temperature. The reaction solution was dialyzed (SpectraPor 4 (manufactured by Spectrum), molecular weight cutoff (MWCO): 12,000 to 14,000) successively against 0.3M ammonia acetate/DMSO solution, an aqueous solution of 0.15M NaCl, and ultrapure water. Ethylene glycol (EG) was added to the resultant dialysate such that the amount thereof in the composition became 0.0062 ppm by mass, and the resultant was lyophilized to obtain an intended product (HA-C$_6$-Chol) as a white solid. The $^1$H-NMR spectrum of the resultant is shown in FIG. 3. A peak derived from acetyl group in N-acetyl-D-glucosamine (COCH$_3$, 1.6 ppm to 2.0 ppm, 3H) and a peak derived from methyl group in choles-teryl group (CH$_3$, 0.7 ppm, 3H) were confirmed.

Examples 2 to 25 and Comparative Examples 1 and 2

(Preparation of Hyaluronic Acid Derivative Compositions HA-a2 to HA-a25 and HA-b1 and HA-b2)

Each hyaluronic acid derivative composition was obtained by the same method as Example 1, except that, in the "3. Step 3", the addition amount of Chol hydrochloride relative to HA units and the addition amount of DMT-MM relative to HA units were changed to satisfy the molar ratio shown in the following tables and the type of alcohol and the amount of the polar group-containing compound (B) relative to the hyaluronic acid derivative (A) were changed as shown in the following tables. Each resulting hyaluronic acid derivative composition was subjected to $^1$H-NMR measure-ment, thereby confirming that both a peak derived from acetyl group in N-acetyl-D-glucosamine (COCH$_3$, 1.6 ppm to 2.0 ppm, 3H) and a peak derived from methyl group in cholesteryl group (CH$_3$, 0.7 ppm, 3H) were present in the hyaluronic acid derivative contained in each hyaluronic acid derivative composition.

In the following tables, the type and abbreviation of alcohol are as follows.

(Type and Abbreviation of Alcohol)

Isopropanol: IPA

Ethanol: ETOH

Each physical property of hyaluronic acid derivative compositions obtained in examples and comparative examples was measured and evaluated diversely by the above-mentioned methods. Results are shown in the follow-ing tables.

TABLE 1

| | | Example 1 | Example 2 | Example 3 | Example 4 | Example 5 |
|---|---|---|---|---|---|---|
| | HA derivative composition | HA-a1 | HA-a2 | HA-a3 | HA-a4 | HA-a5 |
| Cons-titu-tion | Molecular weight of HA | 50 kDa | 50 kDa | 50 kDa | 50 kDa | 50 kDa |
| | Molar ratio of HA unit/Chol hydrochloride/ DMT-MM | 100/ 15/ 21.6 | 100/ 15/ 21.6 | 100/ 15/ 21.6 | 100/ 15/ 21.6 | 100/ 15/ 21.6 |
| | Introduction ratio of steryl group (%) | 15 | 15 | 15 | 15 | 15 |
| | Type of alcohol | EG | EG | EG | EG | IPA |
| | Amount of alcohol relative to HA derivative (ppm by mass) | 0.0062 | 10 | 60 | 99 | 0.0062 |
| Eval-ua-tion | Precipitation ratio (%) of HA derivative composition | 85.4 | 85.5 | 86.2 | 85.6 | 74.5 |

TABLE 2

| | | Example 6 | Example 7 | Example 8 | Example 9 | Example 10 |
|---|---|---|---|---|---|---|
| | HA derivative composition | HA-a6 | HA-a7 | HA-a8 | HA-a9 | HA-a10 |
| Cons-titution | Molecular weight of HA | 50 kDa | 50 kDa | 50 kDa | 50 kDa | 50 kDa |
| | Molar ratio of HA unit/Chol hydrochloride/ DMT-MM | 100/ 15/ 21.6 | 100/ 15/ 21.6 | 100/ 15/ 21.6 | 100/ 15/ 21.6 | 100/ 15/ 21.6 |
| | Introduction ratio of steryl group (%) | 15 | 15 | 15 | 15 | 15 |
| | Type of alcohol | IPA | IPA | IPA | EtOH | EtOH |
| | Amount of alcohol relative to HA derivative (ppm by mass) | 10 | 60 | 99 | 0.0062 | 10 |
| Eval-uation | Precipitation ratio (%) of HA derivative composition | 80.3 | 82.2 | 83.9 | 75.3 | 81.2 |

TABLE 3

| | | Example 11 | Example 12 | Example 13 | Example 14 | Example 15 |
|---|---|---|---|---|---|---|
| | HA derivative composition | HA-a11 | HA-a12 | HA-a13 | HA-a14 | HA-a15 |
| Cons-titution | Molecular weight of HA | 50 kDa | 50 kDa | 35 kDa | 35 kDa | 35 kDa |
| | Molar ratio of HA unit/Chol hydrochloride/ DMT-MM | 100/ 15/ 21.6 | 100/ 15/ 21.6 | 100/ 19/ 26.6 | 100/ 19/ 26.6 | 100/ 19/ 26.6 |
| | Introduction ratio of steryl group (%) | 15 | 15 | 19 | 19 | 19 |
| | Type of alcohol | EtOH | EtOH | EG | EG | EG |
| | Amount of alcohol relative to HA derivative (ppm by mass) | 60 | 98 | 0.0062 | 10 | 60 |
| Eval-uation | Precipitation ratio (%) of HA derivative composition | 82.6 | 85.3 | 90.5 | 91.2 | 90.2 |

TABLE 4

| | | Example 16 | Example 17 | Example 18 | Comparative Example 1 |
|---|---|---|---|---|---|
| | HA derivative composition | HA-a16 | HA-a17 | HA-a18 | HA-b1 |
| Cons-titution | Molecular weight of HA | 35 kDa | 50 kDa | 50 kDa | 50 kDa |
| | Molar ratio of HA unit/Chol hydrochloride/ DMT-MM | 100/ 19/ 26.6 | 100/ 12/ 17.3 | 100/ 17/ 24.5 | 100/ 15/ 21.6 |
| | Introduction ratio of steryl group (%) | 19 | 12 | 17 | 15 |

TABLE 4-continued

| | | Example 16 | Example 17 | Example 18 | Comparative Example 1 |
|---|---|---|---|---|---|
| | Type of alcohol | EG | EG | EG | — |
| | Amount of alcohol relative to HA derivative (ppm by mass) | 99 | 0.0061 | 0.0062 | 0 |
| Eval-uation | Precipitation ratio of HA derivative composition (%) | 90.1 | 91.3 | 82.5 | 46 |

TABLE 5

| | | Example 19 | Example 20 | Example 21 | Example 22 | Example 23 |
|---|---|---|---|---|---|---|
| HA derivative composition | | HA-a19 | HA-a20 | HA-a21 | HA-a22 | HA-a23 |
| Cons-titu-tion | Molecular weight of HA | 100 kDa | 100 kDa | 100 kDa | 100 kDa | 100 kDa |
| | Molar ratio of HA unit/Chol hydrochloride/DMT-MM | 100/15/21.6 | 100/15/21.6 | 100/6/8.64 | 100/20/28.8 | 100/15/21.6 |
| | Introduction ratio of steryl group (%) | 15 | 15 | 6 | 20 | 15 |
| | Type of alcohol | EG | EG | EG | EG | EG |
| | Amount of alcohol relative to HA derivative (ppm by mass) | 0.0064 | 60 | 0.0064 | 0.0063 | 700 |
| Eval-uation | Precipitation ratio (%) of HA derivative composition | 48.8 | 46.6 | 50.9 | 25.1 | 50.3 |
| | Maximum amount of filtration (mL/cm$^2$) | 8.22 | — | — | | 1.74 |

TABLE 6

| | | Example 24 | Example 25 | Comparative Example 2 |
|---|---|---|---|---|
| | HA derivative composition | HA-a24 | HA-a25 | HA-b2 |
| Cons-titution | Molecular weight of HA | 100 kDa | 100 kDa | 100 kDa |
| | Molar ratio of HA unit/Chol hydrochloride/DMT-MM | 100/15/21.6 | 100/15/21.6 | 100/15/21.6 |
| | Introduction ratio of steryl group (%) | 15 | 15 | 15 |
| | Type of alcohol | EtOH | IPA | — |
| | Amount of alcohol relative to HA derivative (ppm by mass) | 0.0064 | 0.0065 | 0 |
| Eval-uation | Precipitation ratio (%) of HA derivative composition | 24.3 | 23.9 | 12.4 |
| | Maximum amount of filtration (mL/cm$^2$) | | | — |

As shown in Tables 1 to 4, when the molecular weight of hyaluronic acid was 50 kDa, the precipitation ratios of the alcohol-containing hyaluronic acid derivative compositions HA-a1 to HA-a12, HA-a17 and HA-a18 (Examples 1 to 12, 17 and 18) in 6 mg/mL NaCl-containing concentrated buffer was favorably within a range of 74.5% to 91.3%. On the other hand, the precipitation ratio of the alcohol-free hyaluronic acid derivative composition HA-b1 (Comparative Example 1) in 6 mg/mL NaCl-containing concentrated buffer was unfavorably 46.0%.

Furthermore, among the hyaluronic acid derivative compositions HA-a1, HA-a17 and HA-a18 (Examples 1, 17 and 18), in which the introduction ratios of steryl groups were different from each other, the precipitation ratios thereof in 6 mg/mL NaCl-containing concentrated buffer tended to become favorable in accordance with the decrease in the introduction ratio of steryl group.

As shown in Tables 5 and 6, when the molecular weight of hyaluronic acid was 100 kDa, the precipitation ratios of the alcohol-containing hyaluronic acid derivative compositions HA-a19 to HA-a25 (Examples 19 to 25) in a low-concentration of 1.2 mg/mL NaCl-containing concentrated buffer were favorably within a range of 23.9% to 50.9%. On the other hand, the precipitation ratio of the alcohol-free hyaluronic acid derivative composition HA-b2 (Comparative Example 2) in 1.2 mg/mL NaCl-containing concentrated buffer was unfavorably 12.4%.

Furthermore, among the hyaluronic acid derivative compositions HA-a19 and HA-a23 (Examples 19 and 23), in which the amounts of alcohol were different from each other, the maximum amounts of filtration thereof tended to be increased in accordance with the decrease in the amount of alcohol.

Furthermore, among the hyaluronic acid derivative compositions HA-a23 to HA-a25 (Examples 23 to 25), in which the amounts of alcohol were different from each other, the precipitation ratio thereof in 1.2 mg/mL NaCl-containing concentrated buffer was favorable when ethylene glycol was used.

INDUSTRIAL APPLICABILITY

The hyaluronic acid derivative composition according to the present embodiment makes it possible to provide a hyaluronic acid derivative composition having an excellent precipitation forming ability under a physiological saline concentration, a pharmaceutical composition containing the same, and a hyaluronic acid derivative-drug conjugate composition.

The invention claimed is:

1. A hyaluronic acid derivative composition comprising:
a hyaluronic acid derivative (A) in which a steryl group is introduced; and
a polar group-containing compound (B) selected from the group consisting of ethanol, isopropanol, and ethylene glycol,
wherein an introduction ratio of the steryl group is 0.1% to less than 35% relative to the hyaluronic acid derivative (A),
  wherein an amount of the polar group-containing compound (B) relative to a mass of the hyaluronic acid derivative (A) is 0.001 ppm by mass to less than 700 ppm by mass,
wherein the hyaluronic acid derivative (A) has a molecular weight of in the range of 1,000 to less than 1,000,000, and
wherein the hyaluronic acid derivative (A) comprises a repeating unit of general formula (I):

(I)

wherein $R^1$, $R^2$, $R^3$, and $R^4$ are each independently selected from the group consisting of a hydrogen atom, $C_{1-6}$ alkyl, formyl, and $C_{1-6}$ alkylcarbonyl;
Z is a direct bond or a peptide linker consisting of 2 to 30 amino acid residues;
$X^1$ is a group selected from group consisting of:
  —$NR^b$—R,
  —$NR^b$—COO—R, —$NR^b$—CO—R,
  —$NR^b$—CO—$NR^c$—R,
  —COO—R,
  —O—COO—R,
  —S—R,
  —CO—$Y^a$—S—R,
  —O—CO—$Y^b$—S—R,
  —$NR^b$—CO—$Y^b$—S—R, and
  —S—S—R,
wherein $R^a$, $R^b$ and $R^c$ are each independently selected from the group consisting of a hydrogen atom, $C_{1-20}$ alkyl, amino $C_{2-20}$ alkyl, and hydroxy $C_{2-20}$ alkyl; wherein a group selected from the group consisting of —O— and —$NR^f$— may be inserted in the alkyl moiety thereof;
$R^f$ is selected from the group consisting of a hydrogen atom, $C_{1-12}$ alkyl, amino $C_{2-12}$ alkyl, and hydroxyl $C_{2-12}$ alkyl; wherein a group selected from the group consisting of —O— and —NH— may be inserted in the alkyl moiety thereof;
R is a steryl group;
Y is a $C_{2-30}$ alkylene or —$(CH_2CH_2O)_m$—$CH_2CH_2$—; and a group selected from the group consisting of —O—, —$NR^g$— and —S—S— may be inserted in the alkylene;
$R^g$ is selected from the group consisting of a hydrogen atom, $C_{1-20}$ alkyl, amino $C_{2-20}$ alkyl, and hydroxy $C_{2-20}$ alkyl; wherein a group selected from the group consisting of —O— and —NH— may be inserted in the alkyl moiety thereof;
$Y^a$ is a $C_{1-5}$ alkylene;
$Y^b$ is a $C_{2-8}$ alkylene or a $C_{2-8}$ alkenylene; and
m is an integer of 1 to 100.

2. The hyaluronic acid derivative composition according to claim 1, wherein R is a cholesteryl group.

3. A pharmaceutical composition comprising: a drug; and a carrier, wherein the carrier is a hyaluronic acid derivative composition of claim 1.

4. The pharmaceutical composition according to claim 3, wherein the drug forms a complex with the hyaluronic acid derivative (A).

5. The pharmaceutical composition according to claim 3, wherein the drug is a pharmacologically active protein, a peptide or a nucleic acid.

6. A hyaluronic acid derivative-drug conjugate composition comprising: the hyaluronic acid derivative composition (A) of claim 1; and a drug; wherein the drug is conjugated to the hyaluronic acid derivative (A) in the hyaluronic acid derivative composition.

* * * * *